US011548792B2

(12) United States Patent
Szczepaniak et al.

(10) Patent No.: US 11,548,792 B2
(45) Date of Patent: Jan. 10, 2023

(54) WATER-SOLUBLE GOLD (III) COMPLEXES, METHODS OF PRODUCING WATER-SOLUBLE GOLD (III) COMPLEXES AND THEIR USE

(71) Applicants: Stanislaw Szczepaniak, Kielce (PL); Elwira Szczepaniak, Kielce (PL); Remigiusz Szczepaniak, Kielce (PL); Dominika Szczepaniak, Kielce (PL); Monika Szczepaniak, Kielce (PL)

(72) Inventors: Stanislaw Szczepaniak, Kielce (PL); Elwira Szczepaniak, Kielce (PL); Remigiusz Szczepaniak, Kielce (PL); Dominika Szczepaniak, Kielce (PL); Monika Szczepaniak, Kielce (PL)

( * ) Notice: Subject to any disclaimer, the term of this patent is extended or adjusted under 35 U.S.C. 154(b) by 227 days.

(21) Appl. No.: 16/625,998

(22) PCT Filed: Jul. 4, 2018

(86) PCT No.: PCT/EP2018/068053
§ 371 (c)(1),
(2) Date: Dec. 23, 2019

(87) PCT Pub. No.: WO2019/008013
PCT Pub. Date: Jan. 10, 2019

(65) Prior Publication Data
US 2020/0165141 A1  May 28, 2020

(30) Foreign Application Priority Data
Jul. 4, 2017 (PL) .......................................... 422125

(51) Int. Cl.
C01G 7/00 (2006.01)
A61K 33/242 (2019.01)

(52) U.S. Cl.
CPC ............ *C01G 7/006* (2013.01); *A61K 33/242* (2019.01)

(58) Field of Classification Search
CPC .............................. C01G 7/006; A61K 33/242
See application file for complete search history.

(56) References Cited

U.S. PATENT DOCUMENTS

| 5,603,963 A | 2/1997 | Elder et al. |
| 2018/0208476 A1* | 7/2018 | Lu .......................... C01G 7/006 |

FOREIGN PATENT DOCUMENTS

| PL | 401203 A1 * | 4/2014 |
| PL | 411432 A1 | 9/2016 |

OTHER PUBLICATIONS

Monlien et al., "Cyanide and chloride exchange on homoleptic gold(III) square-planar complexes: variable pressure kinetic investigation by heteronuclear NMR," Inorganica Chimica Acta 331 (2002) 257-269. (Year: 2002).*
Canumalla et al., "Redox and ligand exchange reactions of potential gold(I) and gold(III)-cyanide metabolites under biomimetic conditions," Journal of Inorganic Biochemistry 85 (2001) 67-76. (Year: 2001).*
International Search Report and Written Opinion for Application No. PCT/EP2018/068053, dated Oct. 29, 2018, 9 pages.

* cited by examiner

*Primary Examiner* — Anthony J Zimmer
(74) *Attorney, Agent, or Firm* — Sterne, Kessler, Goldstein & Fox P.L.L.C.

(57) ABSTRACT

The present invention relates to a process for the preparation of a composition comprising a gold (111) chlorite-cyanide coordination compound, a composition comprising the gold (111) compound obtainable by this process, as well as the afore-mentioned composition for use in therapy, more particularly for use in the treatment of cancer.

16 Claims, 7 Drawing Sheets

WATER-SOLUBLE GOLD (III) COMPLEXES, METHODS OF PRODUCING WATER-SOLUBLE GOLD (III) COMPLEXES AND THEIR USE

BACKGROUND

The invention concerns water-soluble, intelligent gold (III) complexes, methods of producing water-soluble, intelligent gold (III) complexes and their use.

Gold has been used in pharmacology and cosmetics since ancient times. Today still using gold preparations is recommended in infectious, rheumatic and venereal diseases, psoriasis, vitiligo, diabetes, collagenosis, angina, epilepsy and neoplasms. Due to its antibacterial, antimycotic and antiviral properties, gold supports the treatment of inflammatory skin conditions, as well as accelerates healing of wounds and burns. Gold also supports functioning of many systems, including the nervous system, as it improves brain function.

Over 70 thousand patents present methods for detection, diagnosis and elimination of neoplastic cells, but none of them is universally effective, and presently we can distinguish over 100 types of cancer.

The researchers from an institute in Cambridge (England) have already identified 475 mutations associated with neoplasms, which translates to approximately 50 thousand different neoplastic diseases. Laboratories and scientific institutions worldwide have researched and patented or implemented in the treatment of neoplasms numerous compounds containing platinum-group metals, gold and other metals. Presently, over 80 various compounds from the platinum group alone are registered, with cisplatin and its derivatives being the most popular and frequently used in chemotherapy.

In 1965, Barnett Rosenberg unexpectedly discovered antineoplastic properties of cisplatin (diamminedichloroplatinum II), which was the first preparation in the group of coordination compounds of divalent platinum (II). On 19 Dec. 1978, following years of studies, Food and Drug Administration (FDA) registered cisplatin as a chemotherapeutic agent for the treatment of genitourinary neoplasms.

Due to this discovery, the interest in coordination compounds of platinum (II) and other transient metals increased.

Presently, approximately 70% of all chemotherapy cases involve antineoplastic therapies with the use of platinum, and one of the medicinal products containing platinum (II) is Cisplatin-"Ebewe". According to the information from the manufacturer, the product is indicated in a multi-drug chemotherapy of advanced neoplasms: lung carcinoma, bladder carcinoma, cervical cancer, testicular cancer and ovarian cancer (stages III and IV), as well as head and neck squamous cell carcinoma (palliative treatment). Its mechanism of action consists in cross-linking within and between the DNA particles, which prevents synthesis of the nucleic acid, inhibits cell division (cytostatic effect), and results in the death of the neoplastic cell. The growth and development of the neoplasm is thus inhibited. Cisplatin is recommended at concentrations of 50 to 120 mg/m$^2$ of the body surface area, at 3- or 4-week interval, or 15 to 20 mg/m$^2$ daily, at 3- or 4-week intervals. Average human body surface area is 1.7 m$^2$, which means that the above cisplatin doses should be multiplied by 1.7. Therefore, a maximum daily dose per kilogram of body weight is almost 3 mg. Cisplatin stability in body fluids is low, and the drug is quickly hydrolysed in blood and lymph.

Other preparations based on platinum combined with amino acids, enzymes or peptides are also known, and their mode of action is similar to that of cisplatin. Cisplatin-based products are highly toxic and associated with adverse reactions, including vomiting, inhibited bone marrow formation, immunosuppression, cytopenias, pain and fatigue. Other effects include general exhaustion of the organism, mucositis, alopecia or dermal complications.

The group of gold-containing anticancer drugs is considerably larger than that of platinum-containing products. It includes primarily medications with Au$^0$ metallic gold (of zero valence), according to the particle size also referred to as colloidal gold (nanoparticle gold), with particle size between a few and a few hundred nanometers.

Presently, there are a few dozen patents and patent applications regarding different gold (I) compounds which, according to description, could be used for the treatment of neoplastic diseases and other conditions.

In the analysis of the effectiveness of these compounds not only the particle size, but also the stability of gold (I) compounds in blood should be considered. Contrary to colloidal gold, many gold (I) compounds are soluble in water, which theoretically guarantees their unlimited solubility in the blood and lymph, associated with their unlimited access with blood to the neoplastic cells. However, there are reports of cases where after injection of gold (I) salt only 1-10% of the injected dose reached the target sites, i.e. the neoplasms, while accumulation in other areas was increased. This is a consequence of a relatively low stability of these compounds in specific environments such as blood, lymph or other body fluids. Due to various factors, the compounds were quickly reduced to metallic gold.

Presented below are patents and patent applications describing the use and production of numerous gold (III) compounds—complexes, which are more stable than gold (I).

U.S. Pat. No. 4,921,847 presents gold (III) complexes having a formula AuLX$_3$, where Au represents gold, L is a nitrogen-containing ligand such as an aliphatic amine, an aromatic amine or a heterocyclic amine and X is a chloride. These compounds are useful in the treatment of neoplasms. Gold (III) complexes have been demonstrated to be useful as antiviral, anti-inflammatory, antibacterial and antiparasitic products.

Another patent (U.S. Pat. No. 6,413,495) presents gold (III) complexes of mono-L-aspartyl chlorine e6, or monoglutamyl chlorine e6 or their pharmacologically acceptable salts. The gold (III) complexes are used in the treatment of neoplastic diseases, and in detection and treatment of arteriosclerosis. A method of gold (III) complex production was also presented.

U.S. Pat. No. 7,632,827 presents organic phosphine gold (III) complexes which, administered in therapeutically effective quantities, treat neoplastic and viral diseases, in both in vitro and in vivo studies.

U.S. Pat. No. 8,481,496 demonstrates the use of gold (III) complexes with oligopeptides functionalised with sulfur atoms as antineoplastic agents. Gold (III) complexes of the [Au(III)X$_2$pdtc)] type, containing dithiocarbamato groups are promising antineoplastic drugs, as their toxicity is much lower than that of cisplatin. The description also presented the methods of preparation of the gold (III) complexes with dithiocarbamato ligands and peptides. The shortcoming associated with the preparation of the complexes is the need to use a strongly toxic carbon disulfide (CS$_2$), which requires complicated methods of separation and cleansing.

U.S. Pat. No. 8,530,659 presents a pharmaceutical composition used for the treatment of cancer, involving cyclomethylated carbenes whose central atom is gold (III) or platinum (II). The composition demonstrates an antineoplastic effect, including apoptosis of the neoplastic cells, and exerts a limited toxic effect on human cells.

Another patent, U.S. Pat. No. 8,563,712, presents a method of cancer treatment through histone deacetylase inhibition, which consists in administration of therapeutically effective quantities of Au(III) in an aromatic complex having the formula presented in the picture, or pharmaceutically acceptable salts thereof.

U.S. Pat. No. 8,828,984 describes composition and synthesis of Au(III)-HNC organic complexes for the treatment of cancer, or thiol fluorescent detection. Presented in the patent are also methods of cancer (tumour) treatment and prophylaxis, as necessary, by the administration of Au(III)-NHC complexes, which demonstrate antineoplastic effects: neoplastic cell death due to inhibited proliferation and growth of the tumour in vivo. A serious disadvantage of this invention is the use of strongly toxic $CF_3SO_3^-$ anions.

U.S. Pat. No. 8,885,611 (B1) presentation revealed cytotoxic gold (III) compounds, that is complexes of the type [diaminocyclohexane)AuCl$_2$]Cl derived from sodium tetrachloroaurate (III) dihydrate $NaAuCl_4 \cdot 2H_2O$. Specifically, the cytotoxic compounds are gold complexes of isomers of (1,2-diaminocyclohexane) $AuCl_3$. In order to treat cancer cells in a patient, such as prostate cancer or gastric cancer, an effective amount of the isomer of 1,2-(diaminocyclohexane)$AuCl_3$ is administered at a concentration ranging between about 10 µM and 20 µM (micromoles).

U.S. Pat. No. 9,023,370 presents organic complexes containing heterocyclic O, N and S atoms with gold, silver or platinum nanoparticles, administered in effective amounts by intravenous, subcutaneous or intramuscular injection to mammals, including humans:

U.S. Pat. No. 9,346,832 presents organic gold (III) complexes for the treatment of cancer. It also describes the methods of preparing aliphatic diamine with heterocyclic aldehydes with Schiff base, followed by condensation with tetrahaloaurate (III) quaternary salts. The synthesis of organic gold (III) complexes has many stages, and involves toxic and inflammable solvents.

In U.S. Pat. No. 9,487,542, the gold (III) complexes with mixed diaminocyclohexane and ethylenediamine ligands or their derivatives are presented. The complexes may exist in both cis- and trans-configurations. The patent also presents pharmaceutical compositions containing gold (III), the methods of synthesis, cancer treatment and inhibiting cancer cell proliferation, as well as inducing cancer cell apoptosis. The mixed gold (III) complexes or pharmaceutically acceptable salts are administered at a concentration of 5-50 µM (micromoles) of Au(III).

In U.S. Pat. Nos. 9,585,861 and 9,481,693, the gold (III) complexes with mixed diaminocyclohexane and 1,3-propylenediamine ligands or their derivatives are presented. The patent presents the methods of synthesis, cancer treatment and inhibiting cancer cell proliferation, as well as inducing cancer cell apoptosis. The mixed gold (III) complexes or pharmaceutically acceptable salts are administered at a dose of 0.05-200 mg/kg per body weight of the mammal.

Another patent presentation, U.S. Pat. No. 9,657,035, described a method of cancer treatment involving administration of effective quantities of at least one gold (III) complex with diaminocyclohexane or its derivatives. Gold (III) complexes are represented by formula I, II and III, where the molar ratio of diaminocyclohexane to Au(III) is 2:1. These cation gold (III) complexes are administered with a pharmaceutically acceptable counter ion (anion) in the amount of 1-100 mg/kg.

Patent application EP 0195147 demonstrates a novel class of aminegold (III) complexes in which the nitrogen-containing ligand is an alkylamine, an arylamine or a heterocyclic amine. The above aminegold (III) complexes are useful in the treatment of neoplasms in mammals. The active substance is administered in the amount of 2-480 mg/kg, and it can also be used as a therapeutic agent.

Patent EP 2502627 presents an anti-cancer agent selected from the group of quinoxaline phosphine complexes containing atoms of transition metal, i.e. gold, copper or silver. This new preparation demonstrates a higher antineoplastic activity than previously used cisplatin combined with taxol.

In patent description CA 1,255,673, Au(III) complexes comprise of nitrogen containing ligand and chloride or bromide. Such gold (III) complex is an active neoplasm-treating ingredient. The amine ligand is a heterocyclic compound selected from the group of pyridine, pyridazine, pyrimidine and imidazole. These heterocyclic gold (III) complexes may be administered orally or parenterally in the treatment of malignant neoplasms.

Patent application WO 2010062846 disclosed new aromatic gold (III) complexes, the methods of their synthesis and use. The new complexes were demonstrated to be very stable, which enables using them in the treatment of neoplastic cells. The presentation also provides examples of using these compounds for the inhibition of neoplastic cell growth, and examples of therapeutically effective doses.

Patent application WO 2012157128 presents gold (III) complexes with optically active amides, nonane-1,6-diamine and picoline acid. The complexes demonstrate strong antineoplastic properties, even in small doses. A considerable disadvantage of this invention consists in a very complicated synthesis, involving toxic and inflammable solvents.

Patent application WO 2013005170 presents modulators based on gold (I) and/or gold (III), which selectively bind to the proteins of transmembrane aquaglyceroporins AQP cells. The selective inhibition of AQP channels is accomplished by compounds tetracoordinated to gold (III) complexes. The invention discloses the uses thereof in manufacturing pharmaceuticals, cosmetics and chemical reagents for diagnostics, treatment, prophylaxis and prevention of conditions associated with aquaglyceroporin AQP functions, especially in the treatment of cancer.

Patent application US 2015125550 presents a method of inhibiting the growth of lung cancer cells or glioma (brain tumour) cells by administration of effective quantities of the antineoplastic agent selected from the group comprising 2,9-di-sec-butyl-1,10-phenanthroline; (2,9-di-sec-butyl-1,10-phenanthro line)$AuCl_3$; (2-mono-n-butyl-phenanthroline)$AuCl_3$ and their combinations. Additionally, an anti-cancer platinum-based compound is administered, preferably cisplatin.

Patent application US 2015182489 presents the method of treatment of breast, ovarian, prostate or gastric cancer by the administration of effective quantities of antineoplastic drug. The drug contains monomeric gold (III) in a complex with ethylenediamine in a molar ratio of 1:1, having the formula [Au(en)Cl$_2$]Cl. This gold (III) complex is administered at a dose of 32.3 mg/kg or less daily for 14 days.

The most recent US 2017157261 patent application discloses conjugates, compositions and methods that include or use one or more gold (III) porphyrin complex. The preferred conjugates are gold (III) porphyrin-poly(ethylene glycol)

(PEG) compounds. Disclosed are the methods for the treatment of cancer comprising administering to a human a therapeutically effective amount of gold (III) porphyrin-poly (ethylene glycol) (PEG) conjugates. The conjugates can be in the form of nanostructures formed by self-assembly of the gold (III) porphyrin-PEG conjugates, or nanocomposites formed by encapsulation of other therapeutic agents by the nanostructures of gold (III) porphyrin-PEG conjugates.

From Chinese patent CN 102268003 presentation we learn about asymmetrical gold (III) porphyrins as antineoplastic agents, and the methods of their preparation. Asymmetrical porphyrins are obtained as a result of reaction between pyrrole and various aromatic aldehydes, followed by a reaction with gold (III) salts. The newly synthesised gold (III) complexes demonstrate an improved ability to inhibit the development of neoplastic cells compared to the usually applied cisplatin.

The Chinese CN 102368027 application presents gold (III) complexes with aromatic or aliphatic picoline acid amides, which demonstrate antineoplastic activity and can be used for the treatment of neoplasms.

Patent CN 103385851 description presents injectable drugs for cancer patients. The composition contains bis-[2,3-bis (tert-butyl methyl phosphonate) quinoxaline] gold (III) chloride. Moreover, the composition contains a pharmaceutically acceptable surfactant. The weight ratio between the complex and the surfactant is 1:1-50.

Patent CN 103547269 description presents quinoxaline phosphine complexes with a transition metal atom selected from the group: gold, copper and silver, in combination with cyclodextrin compounds. The new complexes demonstrate a good solubility and high antineoplastic activity. Their shortcomings include complicated synthesis and toxic reagents.

In most cases, the above organic gold (III) complexes are very poorly soluble in water. It is well known that all cells, including the neoplastic cells, are nourished by the ingredients in blood, and approximately 90% of blood is water, as well as 83% of lungs, 79% of kidneys, 88% of brain, 73% of heart and 71% of liver is water. Therefore, good active substance used in systemic therapy should demonstrate a very good solubility and stability in water, especially in blood and lymph.

Solubility of the active substance in water is of great importance in the treatment of neoplastic diseases. Neoplastic cells may disperse through blood and/or the lymphatic system to local lymph nodes and to distant sites, creating metastases, i.e. secondary tumours developing in organs and tissues often considerably distant from the primary tumour site. Secondary tumours are very difficult to treat, as they can quickly infiltrate numerous tissues and organs, making simultaneous treatment difficult, and often impossible. Metastases frequently occur even several years after a seemingly successful chemotherapy, radiotherapy or surgical removal of the primary tumour.

The dominant features which should characterise a good antineoplastic preparation include: possibly high therapeutic effectiveness, possibly low toxicity, solubility in water, stability and the active substance molecule smaller than 1 nanometre (nm).

Polish patent application PL 411432 presented water-soluble, intelligent gold (III) complexes, methods of their preparation and their use as an independent agent or an ingredient of a pharmaceutical product in a therapeutically justified quantity, and using any route of administration in neoplastic diseases. The cyanide complexes of, preferably, gold (III) mono-, di-ions are obtained in a aqueous or hydro-alcoholic solution in a reaction between cyanide and monovalent alkaline metal in a molar ratio of 1:3 to 1:6.

The gold (III) complexes described in PL 411432 are durable and additionally stabilised with chloride dioxide, but do not possess certain important properties described below. As it is commonly known, neoplastic cells ferment glucose to lactic acid that acidifies mammalian organism and thus hinders the process of combating neoplastic cells by immune cells such as lymphocytes and the so-called natural killer cells (NK). Moreover, lactic acid works like biological scissors—it dissolves cellular membranes of neighbouring healthy cells. The organism defends itself against decreasing pH through buffering reactions, which consist in making use of calcium and magnesium ions contained in bones, which it later sends to acidic neoplastic cells. This is evidenced by in vivo study results conducted on animals. They have shown occurrence of calcium and magnesium deposits in places where neoplastic tumours had been before the therapy. In the case when these ions are not delivered with the applied active substance they are shifted to the area of the neoplastic tumour from bones. This can put a serious strain on the skeletal system, as it is significantly weakened in terms of structure (osteoporosis), which is characterised by progressive loss of bone mass, weakening of bone spacious structure, and consequently higher vulnerability to fracture, including spinal damage.

Polish patent application PL 225149 broadly discusses soluble in water, stable gold (III) complexes and the method of their preparation and use for production of dietary supplements or ingredients of dietary supplements, pharmaceuticals and cosmetics, or ingredients in pharmaceutical and cosmetic products. The chloride complexes of gold (III) mono-ions and poly-ions are stabilised with chlorine dioxide.

The chloride complex obtained in accordance with the aforementioned patent is not very durable, especially in the environment of mammalian body fluids. It is captured by thiol-containing amino acids and various nitrogen-containing heterocyclic compounds almost immediately. Therefore, the complexes are not suitable for intravenous, intra-muscular or subcutaneous injections, which is a major drawback in common use.

Similarly, cyanide gold complex (III), presented in patent application PL412005, is not very durable either. It is not stabilised with chloride dioxide and therefore it is prone to reduction by glutathione (GSH) or other thiol-containing amino acids, which is represented in the following reaction

With reference to the above mentioned size of the active molecule, it should be noted that the fine structure of the gold-containing active substance is very important, as it optimises its effectiveness in reaching the tumour. Therefore, fragmentation of the cluster structure which is often formed by the gold molecules is beneficial, as well as the resulting reduction of the size of gold molecules to under 1 nanometre, and preferably to gold (III) mono-ions or di-ions.

Patent DE 3920144 presents in detail the method of obtaining stable, orbitally rearranged monoatomic elements selected from the group consisting of cobalt, nickel, copper, silver, gold, palladium, platinum, ruthenium, rhodium, iridium, and osmium. According to the description, the transformed monoatomic metals can be used in forming catalysts for ceramics, fire-resistant and corrosion resistant materials. Moreover, they demonstrate specific properties, such as high-temperature super-conductivity and the ability to produce energy. This extensive patent description presents the methods (chemical and electrochemical) of obtaining orbitally rearranged, monoatomic gold from large gold clusters from $Au_2Cl_6$ to $Au_{33}Cl_{99}$.

According to the authors of this solution, such activity, consisting in transforming elements to mono-ions, particularly in the case of gold mono-ions, is very important, as it increases the therapeutic effectiveness of the fragmented gold. The diameter of colloidal gold molecules, compared to the diameter of sodium and potassium channels and/or the diameter of openings in cellular membranes and mitochondria, is very large. It is from a few to a few hundred nanometers. Such disproportion prevents easy access of gold molecules ($Au^0$) in blood to neoplastic cells, which significantly reduces the effectiveness of the antineoplastic therapy. The size of colloidal gold molecules results from its tendency to form clusters, that is polymolecular structures composed of joined atoms. Gold clusters contain from several to several dozen atoms of metal, and the metal-metal (Au—Au) distances are identical as in the original, metallic form: they demonstrate a crystallographic structure and have free electrons, as in native gold, and the clusters are so large that they do not pass through the cell membranes of microorganisms or mammals.

Gold clusters form specific cages, whose structure resembles fullerenes. However, most of them are in the shape of pyramid, prism, cone, or take shapes of other three-dimensional structures. Regardless of the structure, the clusters are so large that they do not pass through the cellular and mitochondrial membranes of microorganisms of mammals. For instance, if a cluster is formed from 20 gold atoms with a radius of 0.144 nm each, in the extreme case it will reach the size of 6 nanometers (assuming that it creates a linear structure).

According to studies, over 50% of metallic gold $Au^0$ in the form of large clusters is excreted from the organism in unchanged form within 24 hours from administration, 25-30% is excreted in the next 24 hours, and the remaining part is accumulated in the liver, kidneys and spleen, without the expected therapeutic effect. The studies also demonstrated that injecting empty gold nanoshells (carriers of the active substance) of 20-40 nm results in only 1-10% of the injected dose reaching the target site, that is the neoplasm, while the molecules accumulate in other sites, such as the liver or spleen. In order to improve the gold nanoparticle distribution to the tumour, they were modified in various manners, including combination with antibodies, hormone analogues, macrophages or silicon compounds. There are also gold nanoparticles combined with biologically active peptides and ribonucleic acids (RNA). However, the procedures only slightly improved the effectiveness of penetration into the tumour, as they did not significantly affect the molecule size, and did not reduce the tendency for cluster forming.

On the basis of the above data, it may be concluded that the effectiveness of antineoplastic therapy is closely related to the size of gold molecules and their ability to penetrate into the neoplastic cell.

Referring again to the quoted patent description DE 3920144, to reduce the size of gold clusters, they are repeatedly dissolved in hydrochloric acid with at least a 20 molar excess of sodium chloride in order to break the metal-to-metal binding.

In example 1, activity 8, a solution of monoatomic gold (I) salt $NaAuCl_2.H_2O$ is obtained, with solution pH of approximately 1.0. The monoatomic gold (I) is unstable in time, and in particular it is not resistant to solar light, which causes its rapid disintegration.

$$3Au^{+1} \rightarrow 2Au^0 + Au^{+3}$$

The authors of this invention for years have been conducting intensive research on the methods of producing water-soluble, stable in time, resistant to reduction and solar light gold (III) complexes, easily absorbed by the human organism. Meeting all these conditions required a chemical structure different from the ones presently used and described in the patent literature.

Stability of the substance in various pH environments had to be its primary characteristic. This parameter is necessary for the substance to play its function in the treatment of humans. It is well-known that different pH levels are found in the human organism: from 0.5 to 2 (gastric juice), to 6.3 (saliva), 7.3-7.45 (blood), 7.5-8.8 (bile, pancreatic enzymes). Solubility of the complex compound in all these environments is particularly important if we intend to administer it orally, intravenously of intramuscularly. It is also very important when the treated organ, being the target of systemic drug application, is characterised by a specific pH.

Stability in time and resistance to the solar light are also important. As is known, medicinal products should preferably demonstrate a shelf life of at least 24 months, preferably, however, 36 months. Implementation of the above goals will enable to create a product which can be easily stored, kept in strategic stocks, or used in different climatic conditions. It is also important to make the preparation resistant to reductive factors which may occur in the organism. Due to absence of such stability, many products which were highly effective in laboratory conditions lost all their properties in body fluids following intravenous injection of oral administration. This is illustrated by the example of TAUREDON®, a drug containing aurothiomalate sodium ($Na_2AuSC_4H3O_4$) as the active substance, used in the treatment of rheumatoid arthritis. The drug loses its properties if the iron concentration in the organism is elevated, or if it is in contact with thioaminoacids, ingredients of a protein found in mammalian cells.

The authors of the invention also decided to introduce cyanide groups (—CN) in order to improve the solubility of the complex. They are included in the structure of the invented compound, and their presence is an important characteristic of the compound. As using this function group, often associated with the potent poison potassium cyanide (KCN), may be unexpected, the common presence of this group in food or medicinal products should be demonstrated, and the scope of its harmful effect on living organisms, and the human organism in particular, should be clearly specified.

Common salt (NaCl) is an example of the widespread use of the cyanide group (—CN) in food products. According to many publications, its consumption is necessary for the proper function of the organism. The widely available common salt contains an anticaking agent. Most frequently it is one of the food additives: E 535—sodium ferrocyanide; E 536—potassium ferrocyanide; E 538—calcium ferrocyanide.

The European and Polish standards determine the level of E 536—potassium ferrocyanide in common salt as 20 mg/kg, and in the sea salt as 57 mg/kg. The maximum daily intake of common salt is 75 g, and the average daily intake is 15 g. Consumption of 15 gram of common salt means an intake of 0.3 mg of potassium ferrocyanide, that is approximately 0.13 mg of cyanide. In relation to hydrogen cyanide (HCN), this is the maximum daily dose of the gold (III) complex produced according to this invention, and administered in advanced neoplastic disease. In many cases the dose will be several or several dozen times lower.

The cyanide compounds are used not only as food additives, but also as ingredients of medicinal products. One of them is Antidotum Thalii-Heyl, a drug for radioactive thallium poisoning. Its active substance is iron (III) hexacyanoferrate (II) (Prussian blue) CAS: 14038-43-8. This drug was approved for use in 2003 by FDA—United States Food and Drug Agency. Oral dose of this drug is very high: for children aged 2-12 years of age it is 1 g 3 times a day, and for children over 12 years of age and adults it is 3 g 3 times a day. Continuation of treatment for at least 30 days is recommended. The 9 g of Prussian blue corresponds to a daily intake of over 5,000 mg of hydrogen cyanide (HCN).

Patent PL 225149 disclosed a very simple and safe method of obtaining chlorine (IV) dioxide in a reaction in an aqueous solution of chloroauric (III) acid with sodium chlorite (III) in the presence of at least 20 moles of sodium chloride, conducted even at room temperature.

In this chemical transformation (disproportionation) one atom of trivalent chlorine is reduced to hydrochloric acid (Cl-1), while four atoms of trivalent chlorine are oxidised to chlorine (IV) dioxide. The reaction of preparing water-soluble, stable gold (III) complexes with chlorine (IV) dioxide is presented in the formula below:

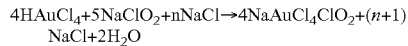

$$4HAuCl_4 + 5NaClO_2 + nNaCl \rightarrow 4NaAuCl_4ClO_2 + (n+1)NaCl + 2H_2O$$

The disclosed complex of gold (III) and chlorine dioxide in sodium chloride (I) solution unexpectedly proved to be very stable during long periods of storage, even in transparent packaging and exposed to the solar light, as well as resistant to freezing and defrosting.

As a result of long tests and studies, it appeared that very fine, mono-ion gold (I) can be easily oxidised with chlorite (III) to favourable gold (III) ions, which may be effectively stabilised with chlorine (IV) dioxide, and subsequently, in the presence of chlorine (IV) dioxide, they may react with a divalent alkaline earth metal cyanide in a proper molar ratio. The alkaline earth metals from the II group of the periodic table of elements include beryllium, strontium, barium and radium, as well as magnesium and calcium, favourably harmless for people and other mammals.

A detailed analysis of the data regarding the quantities of gold acceptable for the human organism for therapeutic purposes, and the toxicity of the cyanide group (CN) stabilised with chlorine dioxide (ClO$_2$) inspired the authors of this invention to create water-soluble, intelligent gold (III) complexes whose therapeutic properties have been confirmed in experimental studies.

OBJECTS AND SUMMARY

Main Objects

It is an object of the present invention to provide a process for the preparation of a composition comprising a gold(+III) compound.

It is another object of the present invention to provide a composition comprising a gold(+III) compound, which is obtainable by the above-mentioned process.

It is yet another object of the present invention to provide the above-mentioned composition comprising a gold(+III) compound for use in therapy, more particularly for use in the treatment of cancer, even more particularly for use in the treatment of colon cancer.

The above objects can be achieved by the aspects described in the following.

It is noted that the present application discloses two ways of formulating the process for the preparation of a composition comprising a gold(+III) compound.

The First Aspect A

In the first aspect A, the present invention relates to a process for the preparation of a composition comprising a gold(+III) compound comprising the steps of:

a) mixing a mixture A comprising a digold(+III) halide and/or gold(+III) halide with a mixture B comprising an alkali halide to create a product mixture 1 or providing commercially available NaAuCl$_4$ and mixing the same with water in order to obtain a product mixture 1;

b) mixing product mixture 1 with hydrochloric acid to create a product mixture 2 c) adjusting the pH of product mixture 2 to a pH value of from 2 to 7;

d) mixing product mixture 2 with a mixture C comprising an alkali chlorite to create a product mixture 3;

e) adjusting the pH of product mixture 3 to an pH of from 5 to 9;

f) mixing product mixture 3 with a mixture D comprising an alkaline earth cyanide to create a product mixture 4;

g) mixing product mixture 4 with an acid to create a product mixture 5, and subjecting product mixture 5 to reduced pressure; and h) adjusting the pH of product mixture 5 to a value of 7 to 8 to obtain a composition comprising a gold(+III) compound.

In an embodiment thereof, the digold(+III) halide and/or gold(+III) halide is a digold(+III) chloride and/or gold(+III) chloride and/or the alkali halide is sodium chloride.

In another embodiment thereof, the mixing of mixture A with mixture B of step a) is effected over a time period of from 1 min to 48 h, preferably from 1 h to 24 h, and more preferably from 5 h to 18 h, and most preferably from 8 h to 12 h, and/or the mixing of step a) is effected at a reaction temperature of from 20° C. to 200° C., preferably from 50° C. to 150° C., most preferably from 80° C. to 120° C.

In yet another embodiment thereof, step a) further comprises step a1) of admixing water to mixture A and/or mixture B, and/or mixture A and/or mixture B further comprise water.

In yet another embodiment thereof, step a) further comprises a step a2) of evaporating the water of product mixture 1 to obtain a product mixture 1A.

In yet another embodiment thereof, step a) further comprises a step a3) of adding water to product mixture 1A to obtain a product mixture 1B.

In yet another embodiment thereof, the hydrochloric acid of step b) is an aqueous solution of hydrochloric acid having a concentration of from 0.1M to 12M, preferably of 2M to 10M, and most preferably of from 5M to 7M.

In yet another embodiment thereof, step b) further comprises a step b1) of evaporating the water of product mixture 2 to obtain a product mixture 2A, and a step b2) of adding water to product mixture 2A to obtain a product mixture 2B.

In yet another embodiment thereof, the pH is adjusted in step c) with a hydroxide base, preferably sodium or potassium hydroxide, and/or the pH is adjusted to a value of from 3 to 6, and preferably from 4 to 5.

In yet another embodiment thereof, the alkali chlorite of mixture C is sodium chlorite, and/or the amount of alkali chlorite used in mixture C and the amount of the gold(+III)

compound(s) used in mixture A have a molar ratio of from 10:1 to 1:2, preferably from 5:1 to 1:1, and most preferably from 3:1 to 1.5:1.

In yet another embodiment thereof, the mixing of step d) is carried out for at least 1 h, preferably at least 3 h, more preferably at least 5 h, even more preferably at least 8 h, and most preferably at least 10 h.

In yet another embodiment thereof, mixture C further comprises water and the alkali chlorite is present in a weight amount of 0.1 wt. % to 10 wt. %, preferably from 0.5 wt. % to 5 wt. %, and most preferably from 0.5 wt. % to 3 wt. %, based on the total weight of mixture C.

In yet another embodiment thereof, the pH is adjusted in step e) with a carbonate base, preferably sodium hydrogen carbonate, and/or the pH is adjusted to a value of from 6 to 8, and preferably from 7 to 8.

In yet another embodiment thereof, the alkaline earth cyanide of mixture D is selected from the group consisting of magnesium cyanide, calcium cyanide, or a mixture thereof, and/or mixture D further comprises water and/or an organic solvent. In a particularly preferred embodiment, the alkaline earth cyanide of mixture D is magnesium cyanide.

In yet another embodiment thereof, mixture D has a concentration of alkaline earth cyanide of from 0.01M to 5M, preferably of 0.01M to 2M, and most preferably of from 0.03M to 1.2M, and/or the amount of alkaline earth cyanide used in mixture D and the amount of the gold(+III) compound(s) used in mixture A have a molar ratio of from 10:1 to 1:2, preferably from 6:1 to 1:1, and most preferably from 4:1 to 2:1.

In a preferred embodiment thereof, residual free cyanide is removed, preferably by a complexing step where residual free cyanide is complexed into a non-soluble complex, which is removed.

In yet another embodiment thereof, the acid used in step g) of the process is an aqueous solution of hydrochloric acid, preferably having a concentration of from 0.01M to 6M, more preferably from 0.05M to 2M, and most preferably from 0.08M to 0.2M.

In yet another embodiment thereof, the product mixture 5 of step g) of the process is subjected to a decreased pressure of from 1 mbar to 950 mbar, preferably from 250 mbar to 900 mbar, and most preferably from 500 mbar to 900 mbar.

In yet another embodiment thereof, the product mixture 5 of step g) of the process is subjected to a decreased pressure of from 1 mbar to 950 mbar, preferably from 250 mbar to 900 mbar, and most preferably from 500 mbar to 900 mbar, until no more hydrogen cyanide evolves from the mixture.

In yet another embodiment thereof, the pH is adjusted in step h) with a phosphate buffer, preferably tetrapotassium diphosphate, and/or the pH is adjusted to a value of from 7.3 to 7.5.

The First Aspect B

In the first aspect B, the present invention relates to a process for the preparation of a composition comprising a gold(+III) compound comprising the steps of:
a) providing a mixture A comprising a tetrachloroaurate salt,
b) mixing the composition of step a) with a mixture B comprising a chlorite salt;
c) mixing the composition obtained in step b) with a mixture C comprising an alkaline earth cyanide to obtain a composition comprising a gold (+III) compound.

In a particularly preferred embodiment thereof, the process comprises the steps of:
a) providing a mixture A comprising a tetrachloroaurate salt and mixing said mixture A comprising a tetrachloroaurate salt with hydrochloric acid,
b) mixing the composition obtained in step a) with a mixture B comprising a chlorite salt;
c) mixing the composition obtained in step b) with a mixture C comprising an alkaline earth cyanide to obtain a composition comprising a gold (+III) compound.

Mixture A as described above in the first aspect B may be produced by a process comprising the following step(s):
step I): mixing a first composition comprising a digold(+III) halide and/or gold(+III) halide with a second composition comprising an alkali halide. In a preferred embodiment of step I), the digold(+III) halide and/or gold(+III) halide is a digold(+III) chloride and/or gold(+III) chloride and/or the alkali halide is sodium chloride, more preferably sodium chloride. It is particularly preferred that the molar ratio of the alkali halide to the tetrachloroaurate salt is at least 100.

In another preferred embodiment of step I), the mixing of the first and second composition is effected over a time period of from 1 min to 48 h, preferably from 1 h to 24 h, and more preferably from 5 h to 18 h, and most preferably from 8 h to 12 h, and/or the mixing of the first and second composition is effected at a reaction temperature of from 20° C. to 200° C., preferably from 50° C. to 150° C., most preferably from 80° C. to 120° C.

In yet another preferred embodiment of step I), the first and/or second composition as described above further comprises water. In another preferred embodiment, the process for producing mixture A further comprises a step II) of evaporating the water of the composition obtained in step I). In another preferred embodiment, the process for producing mixture A further comprises a step III) of adding water to the composition obtained in step II).

In yet another embodiment of the process described above in the first aspect B, mixture A further comprises water.

In yet another embodiment thereof, the tetrachloroaurate salt of mixture A is an alkali tetrachloroaurate salt, and preferably sodium tetrachloroaurate or a hydrated version thereof, and/or mixture A further comprises an alkali halide, preferably sodium halide.

In yet another embodiment thereof, the hydrochloric acid of step a) is an aqueous solution of hydrochloric acid having a concentration of from 0.1M to 12M, preferably of 2M to 10M, and most preferably of from 5M to 7M. It is appreciated by a skilled person that the amount of HCl needed for the reaction to finalize may also be indicated by the colour of the reaction mixture. In case a change in colour is no longer observed upon addition of HCl, the reaction is usually completed.

In yet another embodiment thereof, the process further comprises a step a1) of evaporating the water of the composition obtained in step a), and a step a2) of adding water to the composition obtained in step a1).

In yet another embodiment thereof, the process further comprises a step a3) of adjusting the pH of the composition as obtained in step a), a1) or a2) to a pH value of from 2 to 7, preferably from 3 to 6, and more preferably from 4 to 5.

In another embodiment thereof, the pH is adjusted in step a3) by using a hydroxide base, preferably sodium or potassium hydroxide.

In yet another embodiment thereof, the chlorite salt of mixture B is an alkali chlorite, preferably a sodium chlorite, and/or the amount of the chlorite salt used in mixture B and the amount of the gold(+III) compound used in mixture A have a molar ratio of from 10:1 to 1:2, preferably from 5:1 to 1:1, and most preferably from 3:1 to 1.5:1.

In yet another embodiment thereof, the mixing of step b) is carried out for at least 1 h, preferably at least 3 h, more preferably at least 5 h, even more preferably at least 8 h, and most preferably at least 10 h.

In yet another embodiment thereof, mixture B further comprises water and/or the chlorite salt is present in a weight amount of 0.1 wt. % to 10 wt. %, preferably from 1 wt. % to 5 wt. %, and most preferably from 2 wt. % to 3 wt. %, based on the total weight of mixture B.

In yet another embodiment thereof, the process further comprises a step b1) of adjusting the pH of the composition as obtained in step b) to a pH value of from 5 to 9, preferably from 6 to 8, and more preferably from 7 to 8.

In another embodiment thereof, the pH value is adjusted in step b1) by using a carbonate base, preferably sodium hydrogen carbonate.

In yet another embodiment thereof, the alkaline earth cyanide of mixture C is selected from the group of magnesium cyanide, calcium cyanide, or a mixture thereof, and preferably is magnesium cyanide, and/or mixture C further comprises water and/or an organic solvent.

In yet another embodiment thereof, mixture C has a concentration of alkaline earth cyanide of from 0.01M to 5M, preferably of 0.05M to 2M, and most preferably of from 0.08M to 1.2M, and/or the amount of alkaline earth cyanide used in mixture C and the amount of the gold(+III) compound used in mixture A have a molar ratio of from 10:1 to 1:2, preferably from 6:1 to 1:1, and most preferably from 4:1 to 2:1.

In a preferred embodiment, residual free cyanide is removed, preferably by a complexing step where residual free cyanide is complexed into a non-soluble complex, which is removed.

In yet another embodiment thereof, the process further comprises a step d) of mixing the composition obtained in step c) with an acid, preferably with an aqueous solution of hydrochloric acid.

In another embodiment thereof, the aqueous solution of hydrochloric acid has a concentration of from 0.01M to 6M, preferably from 0.05M to 2M, and more preferably from 0.08M to 0.2M. In yet another embodiment thereof, the composition obtained in step c) is subjected to reduced pressure, preferably of from 1 mbar to 950 mbar, more preferably from 250 mbar to 900 mbar, and most preferably from 500 mbar to 900 mbar.

In yet another embodiment thereof, the composition obtained in step c) is subjected to reduced pressure, preferably of from 1 mbar to 950 mbar, more preferably from 250 mbar to 900 mbar, and most preferably from 500 mbar to 900 mbar, until no more hydrogen cyanide evolves from the mixture.

In yet another embodiment thereof, the process further comprises a step d) of mixing the composition obtained in step c) with an acid, preferably with an aqueous solution of hydrochloric acid. In another embodiment thereof, the aqueous solution of hydrochloric acid has a concentration of from 0.01M to 6M, preferably from 0.05M to 2M, and more preferably from 0.08M to 0.2M, and simultaneously subjecting the composition obtained in step c) to reduced pressure, preferably of from 1 mbar to 950 mbar, more preferably from 250 mbar to 900 mbar, and most preferably from 500 mbar to 900 mbar.

In yet another embodiment thereof, the process further comprises a step e) of adjusting the pH of the composition obtained in step c) or d) to a pH value of from 7 to 8, preferably from 7.3 to 7.5.

In yet another embodiment thereof, the pH is adjusted in step e) by using a phosphate buffer, preferably tetrapotassium diphosphate.

The Aspects Two to Four

In the second aspect, the present invention relates to a composition comprising a gold(+III) compound, obtainable by the process of the first aspect A or B.

In the third aspect, the present invention relates to a composition comprising a gold(+III) compound according to the second aspect for use in therapy.

In the fourth aspect, the present invention relates to a composition comprising a gold(+III) compound according to the second aspect for use in the treatment of cancer.

It can be preferred that the cancer is selected from the group consisting of melanoma, pancreatic cancer, colorectal cancer, rectal cancer, breast cancer and colon cancer. Colon cancer is particularly preferred for the present invention.

In an embodiment relating to the third and fourth aspect, said composition may be administered intravenously, orally or rectally, wherein an intravenous administration is preferred.

Further Objects

The invention discloses water-soluble, intelligent gold (III) complexes, methods of producing water-soluble, intelligent gold (III) complexes and their use. The water-soluble, intelligent gold (III) complexes according to the invention might be represented by the general formula:

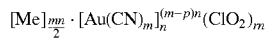

where Me is alkaline earth metal from the II group of the periodic table, favourably magnesium or calcium, m value is from 3 to 6, n value is from 1 to 10, p value is from 1 to 3, and r value is from 0, 1 to 2.

The method of preparing water-soluble, intelligent gold (III) complexes, in which the gold clusters are characteristically dissolved chemically multiple times, preferably in hydrochloric acid (HCl) in the presence of at least 10-molar excess of monovalent chlorides of alkaline earth metals, and each time are evaporated to dryness, until the cluster size is below 1 nanometre, and, preferably, mono-ions or di-ions of gold (III) are obtained, which then undergo a reaction in an aqueous or hydro-alcoholic solution with a cyanide of a divalent alkaline earth metal at a molar ratio from 2:3 to 1:3, preferably in the presence of a mild oxidant, such as chlorine (IV) dioxide or its precursor sodium chlorite (III), whose molar ratio to gold (III) is 0.1 to 2.

The use of water-soluble, intelligent gold (III) complexes having the above formula as an independent medical product or in combination with a pharmaceutical preparation, and/or with a dietary supplement, and/or with a food additive, in therapeutically justified quantities, via any administration route, in neoplastic diseases or other conditions.

DETAILED DESCRIPTION

Main Objects

Figure 1:
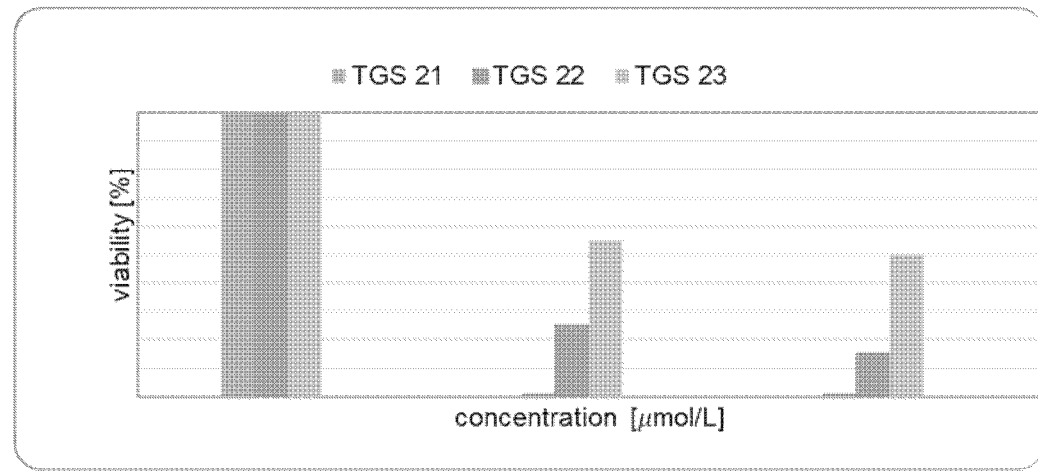
FIG. 1: Viability of melanoma cell line HTB-65 following incubation with TGS 21 (see example 2), TGS 22 (see example 3) and TGS 23 (see example 4). The viability is shown in the y-axis in 100%, wherein each line represents 10% from the bottom to the top (top is 100%). The experiment is described in example 6.

The main objects have been outlined above, wherein the following definitions and additional subject matter apply.

As used in the specification and the claims, the singular forms of "a" and "an" also include the corresponding plurals unless the context clearly dictates otherwise. The same applies for plural forms used herein, which also include the singular forms unless the context clearly dictates otherwise.

The terms "about" and "approximately" in the context of the present invention denotes an interval of accuracy that a person skilled in the art will understand to still ensure the technical effect of the feature in question. The term typically indicates a deviation from the indicated numerical value of ±10% and preferably ±5%.

It needs to be understood that the term "comprising" is not limiting. For the purposes of the present invention, the term "consisting of" is considered to be a preferred embodiment of the term "comprising of". If hereinafter a group is defined to comprise at least a certain number of embodiments, this is also meant to encompass a group which preferably consists of these embodiments only.

Furthermore, if herein a mixture is defined to comprise at least one compound, this is also meant to encompass a mixture which preferably consists of this at least one compound. For example, if a mixture B comprises an alkali halide, this is also meant to encompass a mixture B consisting of an alkali halide, i.e. a mixture B being an alkali halide. A skilled person will thus appreciate that a mixture consisting of a single compound refers to the compound itself.

Unless specified otherwise, the term "evaporating" refers to a process according to which at least a portion of water is removed from a mixture such that a constant weight of the obtained mixture is reached. Moreover, a mixture after evaporation may be defined by its total moisture content which, unless specified otherwise, is less than or equal to 10.0 wt.-%, preferably less than or equal to 5 wt.-%, and most preferably less than or equal to 4 wt.-%, based on the total weight of the mixture after evaporation.

A "digold(+III) chloride" in the meaning of the present invention refers to a compound with the formula $Au_2Cl_6$.

A "alkali halide" or "alkali metal halide" in the meaning of the present invention refers, for example, to LiCl, NaCl, KCl, LiF, NaF, KF, LiBr, NaBr, KBr, LiI, NaI, KI. This list is not meant to be of limiting character.

A "alkaline earth cyanide" or "alkaline earth metal cyanide" in the meaning of the present invention refers to a compound selected from the group consisting of $Be(CN)_2$, $Mg(CN)_2$, $Ca(CN)_2$, $Sr(CN)_2$, $Ba(CN)_2$, or $Ra(CN)_2$.

"Reduced pressure" in the meaning of the present invention refers to a pressure of less than 1013 mbar.

A "molar ratio" of a first and a second compound according to the present invention is to be understood as the ratio of the molar mass of a first compound to the molar mass of a second compound.

The term "pharmaceutically acceptable excipient" as used herein refers to compounds commonly comprised in pharmaceutical compositions, which are known to the skilled person. Examples of suitable excipients are exemplary listed below. Typically, a pharmaceutically acceptable excipient can be defined as being pharmaceutically inactive.

The term "salt" is also meant to encompass hydrated versions of the salt. For example, the term "alkali tetrachloroaurate salt" is also meant to encompass a hydrated version of an alkali tetrachloroaurate salt.

Description of Pharmaceutical Compositions Comprising the Gold(+III) Compound According to the Present Invention A pharmaceutical composition according to the present invention may be formulated for oral, buccal, nasal, rectal, topical, transdermal or parenteral application. Parenteral application is preferred, and includes in particular intravenous administration, but may also be carried out by intraarterial, intratumoral, intrathecal, intravesical, intramuscular or subcutaneous administration.

A pharmaceutical composition of the present invention may also be designated as formulation or dosage form.

The dosage form of the present invention can comprise various pharmaceutically acceptable excipients, which will be selected depending on which functionality is to be achieved for the dosage form. A "pharmaceutically acceptable excipient" in the meaning of the present invention can be any substance used for the preparation of pharmaceutical dosage forms, including coating materials, film-forming materials, fillers, disintegrating agents, release-modifying materials, carrier materials, diluents, binding agents and other adjuvants. Typical pharmaceutically acceptable excipients include substances like sucrose, mannitol, sorbitol, starch and starch derivatives, lactose, and lubricating agents such as magnesium stearate, disintegrants and buffering agents.

The term "carrier" denotes pharmaceutically acceptable organic or inorganic carrier substances with which the active ingredient is combined to facilitate the application. Suitable pharmaceutically acceptable carriers include, for instance, water, aqueous salt solutions, alcohols, oils, preferably vegetable oils, propylene glycol, polyoxyethelene sorbitans, polyethylene-polypropylene block co-polymers such as poloxamer 188 or poloxamer 407, polyethylene glycols such as polyethylene glycol 200, 300, 400, 600, etc., gelatin, lactose, amylose, magnesium stearate, surfactants, perfume oil, fatty acid monoglycerides, diglycerides and triglycerides, polyoxyethylated medium or long chain fatty acids such as ricinoleic acid, and polyoxyethylated fatty acid mono-, di, and triglycerides such as capric or caprilic acids, petroethral fatty acid esters, hydroxymethyl celluloses such as hydroxymethyl, hydroxyethyl, hydroxypropyl, hydroxypropyl acetate succinate, polyvinylpyrrolidone, crosspovidone and the like. The pharmaceutical compositions can be sterile and, if desired, mixed with auxiliary agents, like lubricants, preservatives, stabilizers, wetting agents, emulsifiers, salts for influencing osmotic pressure, buffers, colorings, flavoring and/or aromatic substances and the like which do not deleteriously react with the active compound.

If liquid dosage forms are considered, these can include pharmaceutically acceptable emulsions, solutions, suspensions and syrups containing inert diluents commonly used in the art such as water. These dosage forms may contain e.g. microcrystalline cellulose for imparting bulk, alginic acid or sodium alginate as a suspending agent, methylcellulose as a viscosity enhancer and sweeteners/flavouring agents.

For parenteral application, particularly suitable vehicles consist of solutions, preferably oily or aqueous solutions, as well as suspensions, emulsions, or implants. Pharmaceutical formulations for parenteral administration are particularly preferred and include aqueous solutions of the gold(+III) compound in water-soluble form. Additionally, suspensions of the compounds of the compounds of formula (I) may be prepared as appropriate oily injection suspensions. Suitable lipophilic solvents or vehicles include fatty oils such as sesame oil, soybean oil, or tocopherols, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran.

Particularly preferred dosage forms are injectable preparations. Thus, sterile injectable aqueous or oleaginous suspensions can for example be formulated according to the known art using suitable dispersing agents, wetting agents and/or suspending agents. A sterile injectable preparation can also be a sterile injectable solution or suspension or an emulsion in a non-toxic parenterally acceptable diluent or solvent. Among the acceptable vehicles and solvents that can be used are water and isotonic sodium chloride solution. Sterile oils are also conventionally used as solvent or suspending medium.

Suppositories for rectal administration can be prepared by e.g. mixing the gold(+III) compound with a suitable non-irritating excipient such as cocoa butter, synthetic triglycerides and polyethylene glycols which are solid at room temperature but liquid at rectal temperature such that they will melt in the rectum and release the composition from said suppositories.

For administration by inhalation, the gold(+III) compound according to the present invention may be conveniently delivered in the form of an aerosol spray from pressurized packs or a nebulizer, with the use of a suitable propellant, e.g. dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Oral dosage forms may be liquid or solid and include e.g. tablets, troches, pills, capsules, powders, effervescent formulations, dragees and granules. Pharmaceutical preparations for oral use can be obtained in the form of solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone (crosspovidone), agar, or alginic acid or a salt thereof such as sodium alginate. The oral dosage forms may be formulated to ensure an immediate release or a sustained release of the composition.

A solid dosage form may comprise a film coating. For example, the inventive dosage form may be in the form of a so-called film tablet. A capsule of the invention may be a two-piece hard gelatin capsule, a two-piece hydroxypropylmethylcellulose capsule, a two-piece capsule made of vegetable or plant-based cellulose or a two-piece capsule made of polysaccharide.

The dosage form according to the invention may be formulated for topical application. Suitable pharmaceutical application forms for such an application may be a topical nasal spray, sublingual administration forms and controlled and/or sustained release skin patches. For buccal administration, the compositions may take the form of tablets or lozenges formulated in conventional manner.

As regards human patients, the gold(+III) compound may be administered to a patient in an amount of about 0.001 mg to about 1000 mg per day, preferably of about 0.01 mg to about 100 mg per day, more preferably of about 0.1 mg to about 50 mg per day. It is particularly preferred to administered the gold(+III) compound in an amount of about 0.002/kg to about 0.2 mg/kg body weight, preferably in an amount of about 0.01/kg to about 0.2 mg/kg body weight, more preferably of about 0.02 mg/kg to about 0.04 mg/kg bodyweight.

Further Objects

In pharmaceutical preparations water-soluble, intelligent gold (III) complexes may be used as an independent active substance in the form of aqueous solution, or as an active substance supporting the effect of other drugs useful in the treatment of diseases related to one or more factors from the group including bones, cartilage, joints, veins and arteries, hair, skin, nails, osteoporosis, rheumatic diseases, arterial and venous sclerosis, skin diseases, cardiovascular diseases, allergic diseases, degenerative diseases, eye diseases and various neoplastic diseases, as well as in the treatment of the gastrointestinal, respiratory, vascular, hormonal, excretory, nervous, skin, reproductive, motor and lymphatic systems. These non-organic complexes are preferably used in combination with physiologically acceptable additives, drugs, and chemotherapeutic agents.

The invention may be used independently, for instance as an additive to drinking water and various drinks, or a dietary supplement to supplement gold in human organism, as the element stimulates the mechanism of strengthening one or more human organs from the group comprising bones, cartilage, joints, veins and arteries, as well as hair, nails and skin.

It should be emphasised that the maximum daily therapeutic dose for man might be 0.01 mg/kg/day. Preliminary studies indicate that the most effective therapeutic dose of anionic gold (III) complexes might be below 0.001 mg/kg. In relation to hydrogen cyanide it is approximately 0.0006 mg.

Presence of calcium and/or magnesium ions might prevent or restrict a serious problem related to de-mineralisation of bones or osteoporosis.

Such small doses of anionic gold (III) complexes characterised by good water solubility and stability in systemic fluids are not associated with any hazard for human health.

To sum up, so small, almost homoeopathic doses of gold (III) complexes might selectively destroy neoplastic cells and pathogens harmful for the human organism. The novel method of treatment of neoplastic diseases appears to be so safe that it might be used for the therapy of pregnant women, without the risk of complications for the foetus or the need to make the tragic choice between the life of the mother or the child.

High solubility of anion gold (III) complexes produced according to this invention might be the greatest asset. They might be administered via the oral, intravenous, intramuscular or subcutaneous route, and many of them appear to reach in an intact or unchanged form the receptors, that is the neoplastic cells or other pathogens which present a higher affinity to gold than healthy human cells. Apart from the neoplastic cells, such activity is demonstrated by the pathogens inducing tropical diseases, as well as the borreliosis bacteria, tuberculosis bacteria and many others.

Using chlorine dioxide might stabilise the new compound in the presence of reductive factors found in all live cells, such as thioaminoacids. One of the most common thiols in plant and animal cells is glutathione (GSH). It reduces $Au(CN)_4$ to $Au(CN)_2$, as presented in the reaction below (Journal of Inorganic Biochemistry 85(2001) 67-76)

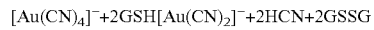

The gold (I) complex appears to be unstable and to quickly be reduced to metallic gold ($Au^0$) before it reaches the antineoplastic cell.

Unexpectedly it appeared that inorganic, anionic, cyanide gold (III) complexes formed in the presence of chlorine dioxide or its precursor, sodium chlorite (III), demonstrate very good solubility in water, blood, plasma and lymph. Importantly, they are also stable in mammalian organisms. They apparently destroy neoplastic cells, as well as the cells of various pathogens, effectively and selectively, in a very short time. Fragmented, favourably mono-ion gold (III) whose ion radius is the smallest of all the platinum-group metals, as well as silver and copper, might even be able to use the sodium/potassium channels to penetrate into every cell or mitochondrion, and combine with the DNA (deoxyribonucleic acid), correcting and fixing it, as needed. The DNA might be modified on a cellular level, and the "record" of the state of healthy organism might be restored from its memory.

Neoplastic cells are always young, as they produce telomerase—an enzyme which inhibits their ageing.

Mono-ion gold (III), which penetrates into the neoplastic cells, might eliminate this enzyme, thus leading to the cell death. Cancer metabolism is 8-20 times faster than that of healthy cells. Moreover, they contain several times more thioaminoacids such as methionine, homocysteine, cysteine and its oxidation product—cystine. Due to all these factors neoplastic cells appear to have a 20-25 times higher affinity to gold than healthy cells; therefore, when absorbable (very fine) gold is administered, it might first be consumed by neoplastic cells. Newly developed, water-soluble gold (III) complexes are referred to as "intelligent", because they can unmistakably find the neoplastic cells and selectively destroy them.

In the neoplastic cells, where pH is slightly acidic (5.0-6.5), the invented compound having the general formula decomposes to a gas $ClO_2$, which disables the diseased cell by its disintegration. The monoatomic oxygen and chlorine produced in situ oxidise the adjacent neoplastic cells. Therefore, even thousandths of a milligram of $ClO_2$ per kg per day might be sufficient to contribute to fighting this dangerous disease. The released gold might correct the DNA, as necessary, and might catalyse oxidation of lactic acid and other organic acids, carbon (II) oxide and glucose to harmless substrates: carbon (IV) dioxide and water. As a result, the pH in the neoplastic cell might be elevated (alkalised), and the cell does not divide, but dies. Certain publications report that "after a contact with mono-ion gold, cancer cells mutate back to normal cells". It would be the most favourable solution, as disintegrating neoplastic tumours and other dead cells would not create toxic burden on the lymphatic system or on other excretory organs, primarily the liver and kidneys.

The gold complex (III) obtained by means of the invention, appears to be characterised by high bio-availability after oral administration, which seems to be 50% of the dose administered by way of intravenous injection. The presence of an active substance, created in accordance with the invention, seemed to be observed as early as 30 minutes after oral administration in kidneys, spleen, liver, lungs and testicles. Particular attention should be attached to the cumulating active substance in the brain, which testifies to its easy transgression of the blood-brain blockage and delivery of an oncological medicine to that formidable area of the body. Furthermore, a high concentration of the substance in the pancreas, lungs and the liver may point to similar conclusions. It also seems that the substance is extracted from the body in nearly 100% after approximately 22 hours. This, together with one of the lowest therapeutic doses reported in literature, which oscillate around 0.02 mg/kg, makes the obtained gold complex (III) one of the most effective antineoplastic formulas in the world. The quantitative analysis of tissue samples was performed by mass spectrometry with inductively coupled plasma.

The newly developed, water-soluble, intelligent gold (III) complexes are very durable, resistant to reduction, stable in time, and in the mammalian organism they are resistant to reduction with glutathione or other thioaminoacids.

Due to significant fragmentation, they are highly effective and can be used in very small quantities as pharmaceutical and cosmetic agents, administered to a mammal at therapeutically justified amounts in any form.

As a cosmetic product, the invention may be used independently in the form of aqueous solution, or in combination, as an ingredient of other cosmetics, for instance creams, ointments, shampoos, gels, tonics, different types of conditioners for the skin, hair and nails, as well as other products for care and regeneration of skin with various disorders, damaged hair and weak nails.

The invention will be explained in details in the examples below, which do not exhaust its potential.

EXAMPLES

Example 1

Preparation of Chlorite-Cyanide Complexes of Mono-Ion Gold (III) Using Magnesium Cyanide (an Alkali Earth Metal Cyanide)

Step a: To a 1 $dm^3$ capacity flask with a stirrer and a condenser we added 200 mg of 99.995% pure metallic gold and dissolved it in aqua regia (mixture of concentrated hydrochloric acid and nitric acid in the molar ratio of 3:1). After being dissolved, gold (III) was in the form of very large clusters with metallic bindings (Au—Au)>10.

Step b: The water-soluble gold clusters (III) obtained in accordance with step a were acidified with 100 $cm^3$ of concentrated (36%) hydrochloric acid (of analytical reagent grade), then the mixture was brought to boil and kept that way until the volume was reduced to 20-30 $cm^3$. After 100 $cm^3$ of concentrated hydrochloric acid has been added again, it was boiled until NOCl (nitrosyl chloride) pairs were released. The action was repeated several times until the effect of no brown smoke and no nitric oxide smell was achieved. This means that the nitric acid and nitric oxides have been vaporised, and only gold chlorides (III) remained in the flask.

Step c: In order to vaporise the liquids (acids) from gold salts (III), a thermostatic polyglycol bath was selected. As the heating medium, polyethylene glycol with molecular weight of 400 with the addition of antioxidants was used. A flask with gold chlorides (III) was placed in the bath mentioned above and vaporised to dry salt. At this stage, it was important that all the liquid was vaporised and the salt was not sintered—it has not changed colour, and, particularly, gold chloride (III) has not been reduced to metallic gold.

Step d: 300 ml of 6 M hydrochloric acid was added to the dry salt and then the lot was heated again to the boiling point of the liquid and vaporised until dry salts remained. This action was repeated 4 times until the smallest possible gold clusters (III) were obtained. At the end of these long-term actions, orange-red gold chloride (III) salt was obtained, whose analysis proved the presence of practically pure $Au_2Cl_6$.

Step e: To $Au_2Cl_6$ thus obtained we added 3 grams of sodium chloride (NaCl) (of analytical reagent grade) (molar ratio of sodium chloride to gold was over 100). Then we replenished it with distilled water until about 500 $cm^3$. Then the lot was boiled for over ten hours and, in the presence of sodium chloride, we obtained $Na_2Au_2Cl_8$. Such a high molar excess of sodium chloride is essential as it facilitates the breakdown of large gold clusters with metallic bindings (Au—Au) and the creation of sodium salt of the monochloroauric acid ($NaAuCl_4$).

Step f: The aqueous solution of sodium chloride and the gold salt was heated until water vaporised and dry salt deposit remained. We then added to the salts 400 $cm^3$ of distilled water and 600 $cm^3$ of 6 M hydrochloric acid in an alternating manner, until no further change of colour was observable.

Step g: After the final 6 M hydrochloric acid treatment and a final vaporisation, dry salts were obtained, which were later dissolved in 250 $cm^3$ of distilled water, by which the solution of single-atom gold salt $HAuCl_2 \cdot H_2O$ was obtained. The solution's pH was approximately 1.0.

Step h: To the flask with such obtained mono-ion gold (I) we carefully added 1 M sodium hydroxide in order to adjust the pH of the solution to pH 4-5. Next, we added 10 g of 1% sodium chlorite (III) ($NaClO_2$)—CAS: 775819-2. The molar ratio of gold to chlorite (III) was 1:2. Molar excess of sodium chlorite (III) was essential to oxidise gold (I) to gold (III) and create the complex. After more than ten hours we obtained a water-soluble, stable gold complex (III) with chloride dioxide and sodium chloride represented by the formula: $NaAuCl_4ClO_2 \cdot (NaCl)_z$, where z amounts to more than 100.

Step i: The mono-ion complex of $NaAuCl_4 \cdot ClO_2 \cdot (NaCl)_z$ was neutralised with 5% sodium hydrogen carbonate ($NaHCO_3$), CAS:497-19-8 to a pH of about 9.0 and then we added 21 $cm^3$ of 0.05 M magnesium cyanide in solution of saline (9 g/$dm^3$ sodium chloride) Molar ratio of mono-ion gold (III) to magnesium cyanide was approximately 1:2. We mixed the lot in the temperature of 50° C. for 4 hours and then, under an intense extract, acidified with 0.1 M hydrochloric acid (HCl). The above synthesis, under decreased pressure, was stirred for 2 hours in order to remove free hydrogen cyanide (HCN). Such highly water-soluble complexes of mono-ion gold (III) were neutralised to pH 7.4 (optimum pH of blood and lymph) by 0.1 M tetrapotassium diphosphate ($K_4P_2O_7$) CAS: 7320-34-5. We replenished the lot with saline the volume of 1 $dm^3$ containing 104 mg of mono-ion gold (III), approximately 0.53 mM, bound into a highly soluble and stable complex.

The synthesis was dissolved tenfold with physiological saline. The concentration of complex of mono-ion gold III was 10.4 mg/$dm^3$ and given the working name "TGS 20".

Example 2

Preparation of Chlorite-Cyanide Complexes of Mono-Ion Gold (III) Using Calcium Cyanide (an Alkali Earth Metal Cyanide)

Step a: To a 1 $dm^3$ capacity flask with a stirrer and a condenser we added 100 mg of 99.99% pure metallic gold and dissolved it in aqua regia (mixture of concentrated hydrochloric acid and nitric acid in the molar ratio of 3:1). After being dissolved, gold (III) was in the form of very large clusters with metallic bindings (Au—Au)>11.

Step b: The water-soluble gold clusters (III) obtained in accordance with step a were acidified with 120 $cm^3$ of concentrated (36%) hydrochloric acid (of analytical reagent grade), then the mixture was brought to boil and kept that way until the volume was reduced to 20-30 $cm^3$. After 120 $cm^3$ of concentrated hydrochloric acid has been added again, it was boiled until NOCl (nitrosyl chloride) pairs were released. The action was repeated several times until the effect of no brown smoke and no nitric oxide smell was achieved. This means that the nitric acid and nitric oxides have been vaporised, and only gold chlorides (III) remained in the flask.

Step c: In order to vaporise the liquids (acids) from gold salts (III), a thermostatic polyglycol bath was selected. As the heating medium, polyethylene glycol with molecular weight of 400 with the addition of antioxidants was used. A flask with gold chlorides (III) was placed in the bath mentioned above and vaporised to dry salt. At this stage, it was important that all the liquid was vaporised and the salt was not sintered—it has not changed colour, and, particularly, gold chloride (III) has not been reduced to metallic gold.

Step d: Dry salts obtained in accordance with the description above were dissolved again in aqua regia, and steps b and c were repeated. The chemical treatment described above allowed to obtain clusters of gold chloride (III) of less than 11 atoms.

Step e: 300 ml of 6 M hydrochloric acid was added to the dry salt and then the lot was heated again to the boiling point of the liquid and vaporised until dry salts remained. This action was repeated 4 times until the smallest possible gold clusters (III) were obtained. At the end of these long-term actions, orange-red gold chloride (III) salt was obtained, whose analysis proved the presence of practically pure $Au_2Cl_6$.

Step f: To $Au_2Cl_6$ thus obtained we added 9 grams of sodium chloride (NaCl) (of analytical reagent grade) (molar ratio of sodium chloride to gold was over 300). Then we replenished it with distilled water until about 500 cm$^3$. Then the lot was boiled for over ten hours and, in the presence of sodium chloride, we obtained $Na_2Au_2Cl_8$. Such a high molar excess of sodium chloride is essential as it facilitates the breakdown of large gold clusters with metallic bindings (Au—Au) and the creation of sodium salt of the monochloroauric acid (NaAuCl$_4$). Eventually, a particularly selected amount of 9 grams of sodium chloride made it possible to obtain an approximate concentration of physiological saline.

Step g: The aqueous solution of sodium chloride and the salt was heated until water vaporised and dry salt deposit remained. We then added to the salts 400 cm$^3$ of distilled water and 600 cm$^3$ of 6 M hydrochloric acid in an alternating manner, until no further change of colour was observable.

Step h: After the final 6 M hydrochloric acid treatment and a final vaporisation, dry salts were obtained, which were later dissolved in 800 ml of distilled water, by which the solution of single-atom gold salt $HAuCl_2.H_2O$ was obtained. The solution's pH was approximately 1.0.

Step i: To the flask with such obtained mono-ion gold (I) we carefully added 1 M sodium hydroxide in order to adjust the pH of the solution to pH 4-5. Next we added 3.8 g of 2.5% sodium chlorite (III) (NaClO$_2$)—CAS: 775819-2. The molar ratio of gold to chlorite (III) was 1:2. Molar excess of sodium chlorite (III) was essential to oxidise gold (I) to gold (III) and create the complex. After more than ten hours we obtained a water-soluble, stable gold complex (III) with chloride dioxide and sodium chloride represented by the formula: $NaAuCl_4.ClO_2.(NaCl)_z$, where z amounts to more than 300.

Step j: The mono-ion complex of $NaAuCl_4.ClO_2.(NaCl)_z$ was neutralised with 2% sodium hydrogen carbonate (NaHCO$_3$), CAS:497-19-8 to a pH of about 7.8 and then we added 16 g of 0.1 M hydroalcoholic solution (water/ethanol) of calcium cyanide—CAS: 592-01-8. Molar ratio of mono-ion gold (III) to calcium cyanide was approximately 1:3. We mixed the lot in the temperature of 30° C. for 2 hours and then, under an intense extract, acidified with 0.1 M hydrochloric acid (HCl). The above synthesis, under decreased pressure (atmospheric pressure), was stirred for 4 hours in order to remove free hydrogen cyanide (HCN). Such highly water-soluble complexes of mono-ion gold (III) were neutralised to pH 7.4 (optimum pH of blood and lymph) by 0.1 M tetrapotassium diphosphate ($K_4P_2O_7$) CAS: 7320-34-5. We replenished the lot with redistilled water to the volume of 1 dm$^3$ containing 100 mg of mono-ion gold (III), approximately 0.5 mM, bound into a highly soluble complex.

The synthesis was dissolved tenfold with physiological saline (9 g/dm$^3$ of sodium chloride) and given the working name "TGS 21".

Example 3

Preparation of Chlorite-Cyanide Complexes of Di-Ion Gold (III) Using Magnesium Cyanide (an Alkali Earth Metal Cyanide)

Step a: To a 1 dm$^3$ capacity flask with a stirrer and a condenser we added 200 mg of 99.99% pure metallic gold and dissolved it in aqua regia (mixture of concentrated hydrochloric acid and nitric acid in the molar ratio of 3:1). After being dissolved, gold (III) was in the form of very large clusters with metallic bindings (Au—Au)>11.

Step b: The water-soluble gold clusters (III) obtained in accordance with step a were acidified with 200 cm$^3$ of concentrated (36%) hydrochloric acid (of analytical reagent grade), then the mixture was brought to boil and kept that way until the volume was reduced to 20-30 cm$^3$. After 200 cm$^3$ of concentrated hydrochloric acid has been added again, it was boiled until NOCl (nitrosyl chloride) pairs were released. The action was repeated several times until the effect of no brown smoke and no nitric oxide smell was achieved. This means that the nitric acid and nitric oxides have been vaporised, and only gold chlorides (III) remained in the flask.

Step c: In order to vaporise the liquids (acids) from gold salts (III), a thermostatic polyglycol bath was selected. As the heating medium, polyethylene glycol with molecular weight of 600 with the addition of antioxidants was used. A flask with gold chlorides (III) was placed in the bath mentioned above and vaporised to dry salt. At this stage, it was important that all the liquid was vaporised and the salt was not sintered—it has not changed colour, and, particularly, gold chloride (III) has not been reduced to metallic gold.

Step d: Dry salts obtained in accordance with the description above were dissolved again in aqua regia, and steps b and c were repeated. The chemical treatment described above allowed to obtain clusters of gold chloride (III) of less than 11 atoms.

Step e: 300 ml of 6 M hydrochloric acid was added to dry salt and then the lot was heated again to the boiling point of the liquid and vaporised until dry salts remained. This action was repeated 4 times until the smallest possible gold clusters (III) were obtained. At the end of these long-term actions, orange-red gold chloride (III) salt was obtained, whose analysis proved the presence of practically pure $Au_2Cl_6$.

Step f: Then we added 18 grams of sodium chloride (NaCl) (of analytical reagent grade) (molar ratio of sodium chloride to gold was over 300). Then we replenished it with distilled water until about 500 cm$^3$. Then the lot was boiled for over ten hours and, in the presence of sodium chloride, we obtained $Na_2Au_2Cl_8$. Such a high molar excess of sodium chloride was essential for an easy breakdown of large gold clusters with metallic bindings (Au—Au) and the creation of sodium salt of the monochloroauric acid (NaAuCl$_4$). Eventually, a particularly selected amount of 18 grams of sodium chloride made it possible to obtain an approximate concentration of physiological saline.

Step g: We neutralised the di-ion complex of Na$_2$Au$_2$Cl$_8$ with 2% sodium hydrogen carbonate to pH 8, added 3 g of 2% sodium (III) chlorate and 26 g of 0.1 M aqueous solution of magnesium cyanide. The molar ratio of gold (III) to cyanide was approximately 2:5. We heated the lot to 35° C. and stirred for 3 hours under intense extract. Then the lot was acidified with 0.1 M phosphoric acid and stirred for 6 hours in order to remove free hydrogen cyanide (HCN). The obtained highly soluble complexes of di-ion gold (III) were neutralised to pH 6.8 with 0.1 M potassium hydroxide. We replenished the lot with redistilled water to the volume of 1 dm$^3$ containing 200 mg of di-ion gold (III) approximately 1 mM, bound into a highly soluble complex.

The synthesis was dissolved twentyfold with physiological saline and given the working name "TGS 22".

Example 4—Comparative Example

Preparation of Chlorite-Cyanide Complexes of Poly-Ion Gold (III) Using Potassium Cyanide (an Alkali Metal Cyanide)

Step a: To a 1 dm$^3$ capacity flask with a stirrer and a condenser we added 50 mg of 99.99% pure metallic gold and dissolved it in aqua regia (mixture of concentrated hydrochloric acid and nitric acid in the molar ratio of 3:1). After being dissolved, gold (III) was in the form of very large clusters with metallic bindings (Au—Au)>11.

Step b: The water-soluble gold clusters (III) obtained in accordance with step a were acidified with 60 cm$^3$ of concentrated (36%) hydrochloric acid (of analytical reagent grade), then the mixture was brought to boil and kept that way until the volume was reduced to 20-30 cm$^3$. After 60 cm$^3$ of concentrated hydrochloric acid has been added again, the synthesis was boiled until NOCl (nitrosyl chloride) pairs were released. The action was repeated until the effect of no brown smoke and no nitric oxide smell was achieved. This means that the nitric acid and nitric oxides have been vaporised, and only gold chlorides (III) remained in the flask.

Step c: In order to vaporise the liquids (acids) from gold salts (III), a thermostatic polyglycol bath was selected. As the heating medium, polyethylene glycol with molecular weight of 300 with the addition of antioxidants was used. A flask with gold chlorides (III) was placed in the bath mentioned above and vaporised to dry salt. This means that all the liquid was vaporised and the salt was not sintered—it has not changed colour, and, particularly, gold chloride (III) has not been reduced to metallic gold.

Step d: Dry salts as obtained were dissolved again in aqua regia, and steps b and c were repeated. The chemical treatment described above allowed to obtain clusters of gold chloride (III) of less than 11 atoms.

Step e: To such obtained dry salt we added 200 cm$^3$ of distilled water, heated the lot to the temperature of 40° C. and stirred until complete dissolution of polychloroauric acids (III). Then we neutralised it with 5% sodium hydrogen carbonate (NaHCO$_3$) to obtain pH of approximately 7.8 and added 4 g of 0.5% sodium chlorite (III). Next, under the extract, we dispensed 20 g of 0.05 M hydroalcoholic solution of potassium cyanide CAS: 151-50-8. Molar ratio of poly-ion gold (III) to potassium cyanide was approximately 1:4. We stirred the lot in the temperature of 25° C. for 2 hours and then acidified with 5% 2-aminoethanesulfonic acid. Next, in vacuum, we stirred for 2 hours in order to remove free cyanides. We neutralised the water-soluble chlorite-cyanide complexes of poly-ion gold (III) with 5% sodium hydrogen carbonate to pH of approximately 6.5. The synthesis above was then replenished with distilled water to the volume of 1 dm$^3$ containing 50 mg of poly-ion gold (III) (approximately 0.25 mM), bound into highly water-soluble anion complexes.

The synthesis was dissolved fivefold with physiological saline and given the working name "TGS 23".

Example 5—Comparative Example

Preparation of Chlorite-Cyanide Complexes of Monoionic Gold (III) Using Sodium Cyanide (an Alkali Metal Cyanide)
This example corresponds to example 1 of patent application PL411432.

a) We put 100 mg of 99.99% pure metallic gold into a 1 dm$^3$ flask with a stirrer and a trickle cooler, and dissolved the gold in aqua regia (a mixture of concentrated hydrochloric and nitric acids at 3:1 molar ratio). After dissolving, gold (III) can be found in the form of very large clusters with (Au—Au)>11 metallic bonds.

b) The water-soluble clusters of gold (III) obtained using the specification above, were acidified using 120 cm$^3$ of concentrated (36%) reagent grade hydrochloric acid, next the mixture was brought to a boil and boiled until its volume decreases up to 20-30 cm$^3$. After repeated addition of 120 cm$^3$ of concentrated hydrochloric acid, the mixture was again brought to a boil, and NOCl (nitrosyl chloride) vapour was released. The aforementioned activity was repeated many times until no brown smoke could be observed and no nitrogen oxides can be smelled. This means that nitric acid and its oxides have completely evaporated, and gold (III) chlorides remained in the flask.

c) To evaporate liquids (acids) from above gold (III) salts, we used specified thermostatic polyglycol bath. Polyethylene glycol with a molecular weight of 400 and added antioxidants, was used as a heating medium. The flask with gold (III) chlorides was placed in the aforementioned bath and evaporated until dry salt was obtained. It is important to evaporate all the liquid and not to sinter the salt (no change in colour), and not to reduce gold (III) chloride to metallic gold.

d) The dry salts obtained using the specification above were dissolved again in aqua regia, repeating, at the same time, steps b and c. The aforementioned chemical treatment makes it possible to obtain clusters of gold (III) chloride consisting of less than 11 atoms.

e) 300 ml of 6 M (molar) hydrochloric acid were added to the dry salt, next the mixture was heated again to the boiling temperature and the liquid was evaporated until dry salts were created. This activity was repeated four times to obtain the smallest possible gold (III) clusters. After concluding these time-consuming activities we obtained an orange-red salt of gold (III) chloride, an analysis of which indicates the presence of practically pure Au$_2$Cl$_6$.

f) To Au$_2$Cl$_6$ obtained in the aforementioned manner, we added 9 grams of reagent grade sodium chloride (the molar ratio between sodium chloride and gold is more than 300 to 1). Next, we added of distilled water to reach approx. 500 cm$^3$. Then the whole was boiled for a dozen or so hours, obtaining, in the presence of sodium chloride, a compound with the formula of Na$_2$Au$_2$Cl$_8$. Such extensive molar surplus of sodium chloride was necessary, as it facilitates the breaking of large gold clusters with metallic (Au—Au) bonds and the creation of sodium chloroaurate (NaAuCl$_4$). To be precise, the selected amount of 9 grams of sodium chloride made it possible to ultimately obtain the concentration of physiological saline solution.

g) The aqueous solution of sodium chloride and the salt was heated, evaporating water, until a dry salt sediment is obtained. Next, the salts were treated alternately with 400 cm$^3$ of distilled water and 600 cm$^3$ of 6 M hydrochloric acid until no further change in colour was observed. 6 M hydrochloric acid was used to treat the salt.

h) After the last treatment using 6 M hydrochloric acid and its final evaporation, we obtained dry salts, which are next diluted in 800 ml of distilled water, thus obtaining a solution of monoatomic gold salt HAuCl$_2$.H$_2$O. The pH of the solution is approx. 1.0.

i) We carefully poured 1 M (molar) sodium hydroxide to the flask with monoionic gold (I), to neutralise the solution to a pH level of 4-5. Next, we added 380 mg of 25% sodium chlorite (III) (NaClO$_2$)—CAS: 7758-19-2. The molar ratio of gold and the chlorite (III) is 1:2. The molar surplus of sodium chlorite (III) is necessary to oxidise gold (I) to gold (III) and form a complex. After a dozen or so hours we obtained a water-soluble, stable gold (III) complex with chlorine dioxide and sodium chloride with the following formula: NaAuCl$_4$.ClO$_2$.(NaCl)$_z$, where z is a number greater than 300.

j) The monoionic NaAuCl$_4$.ClO$_2$.(NaCl)$_2$ complex was neutralised with 2% sodium bicarbonate (NaHCO$_3$), CAS: 497-19-8 up to a pH of approx. 7.8, and next we added 30 g of 0.1M aqueous alcoholic solution of sodium cyanide—CAS:143-33-9. The molar ratio of monoionic gold (III) to cyanide was 1:6. The whole was mixed for 2 hours at a temperature of 30° C., and next, acidified with 0.1M hydrochloric acid (HCl) under a strong fume hood. After that, we mixed the aforementioned synthesis for 4 hours in reduced pressure conditions to expel free hydrogen cyanide (HCN). Such highly water-soluble complexes of monoionic gold (III) were neutralised to a pH of 7.4 (the pH of blood and lymph) using 0.1M sodium hydroxide (NaOH). Next, we added distilled water to reach 1 dm$^3$ containing 100 mg of monoionic gold (III), approx. 0.5 mM (millimole), bound in highly soluble complex.

The synthesis was diluted ten times using physiological saline (9 g/dm3 sodium chloride) and given a working name of "TGS I".

Example 6

The Application of Mono-Ion Gold (III) TGS 21, Di-Ion Gold (III) TGS 22 and Poly-Ion Gold (III) TGS 23 as a Pharmaceutical in a Mammalian Organism The gold (III) complexes obtained in accordance with examples 2 to 4 were compared in terms of influence on the neoplastic cell line of melanoma (MeWO [ATCC HTB-65]) viability. To this aim, a viability assay (a standard XTT assay) was carried out according to the manufacturer's instructions (Sigma Aldrich). Briefly, the cells were seeded in quadruplicates at 8×10$^3$ onto 96-well plates in the volume of 100 ml. After 48 h of culture, either TGS21 or TGS22 or TGS23 was added to the wells at concentrations of 0.06 µmol/L (left columns in FIG. 1), 0.6 µmol/L (middle columns of FIG. 1) and 6 µmol/L (right columns of FIG. 1). Cells treated with solvent only (PBS) were used as control (data not shown). After 48 h of incubation, XTT assay was performed.

The mono-ion gold (III) complex containing calcium—TGS 21—showed the highest, nearly 100% inhibition of neoplastic cell line growth with the concentration of 0.6 µmol/L after 48 hours of incubation. The complexes of di-ion gold (III) containing magnesium—TGS 22—showed a slightly lower efficacy. The potassium-containing poly-ion gold (III) complexes—TGS 23—, on the other hand, were characterised by a decisively lower activity.

FIG. 1 shows the advantage of the mono-ion gold (III) complex with calcium obtained in example 2. The presence of calcium and magnesium (both alkaline earth metals from group II of the periodic table) in the structure of complexes, compared with potassium (alkali metal from group I of the periodic table), has a positive influence on the efficiency of the new compounds.

Example 7

Studies on the MeWo Human Melanoma Cell Line (ATCC HTB-65) Following the Administration of a Gold (III) Complex The Application of Mono-Ion Gold (III) Complex (TGS 21) in an Anti-Neoplastic Therapy as Illustrated by the Case of MeWo Human Melanoma Cell Line The complex or cisplatin was added to cells, which were seeded and cultured under standard conditions in multi-well plates. The viability was determined using the standard assay described in example 6.

Figure 2:
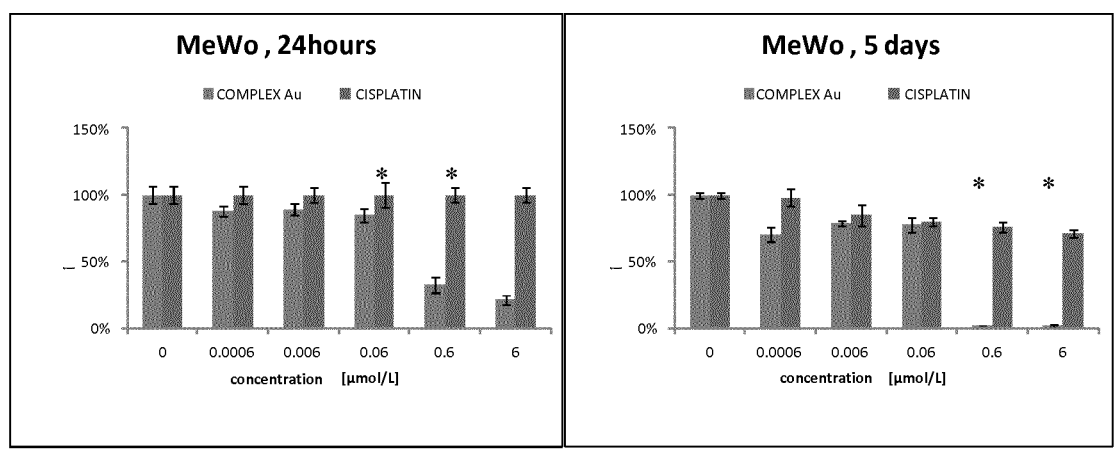
FIG. 2: Viability of the human melanoma cell line (MeWo) following different incubation periods (24 hours and 5 days, as indicated) with TGS 21 (see example 2, referred to as "COMPLEX Au" in the figure) compared to cisplatin. The viability is shown in the y-axis. The experiment is described in example 7.

The studies conducted on the MeWo human melanoma cell line demonstrated a significantly higher biological activity towards the cells than cisplatin used in the same range of concentration, as can be derived from FIG. 2. In the case of this neoplasm the effect was dose-dependent. Growth inhibition was observed already after 24 hours of incubation for the concentrations of 6 and 0.6 µmol/L. Particularly interesting are the results obtained after 5 days of incubation, which reveal that the gold (III) complex demonstrated also activity at the lowest studied concentration, 0.0006 µmol/L. The concentration inhibiting the growth of 50% of cells for the studied compound is between 0.6-6 µmol/L (for 24-hour incubation). It is worth noting that cisplatin, which is the reference substance, in the studied concentration range demonstrated only a weak inhibitory effect.

Example 8

Studies on the B16-F10 Melanoma Murine Cell Line Following the Administration of a Gold (III) Complex The Application of Mono-Ion Gold (III) Complex (TGS 21) in an Anti-Neoplastic Therapy as Illustrated by the Case of B16-F10 Murine Melanoma Cell Line The complex or cisplatin was added to cells, which were seeded and cultured under standard conditions in multi-well plates. The viability was determined using the standard assay described in example 6.

Figure 3:
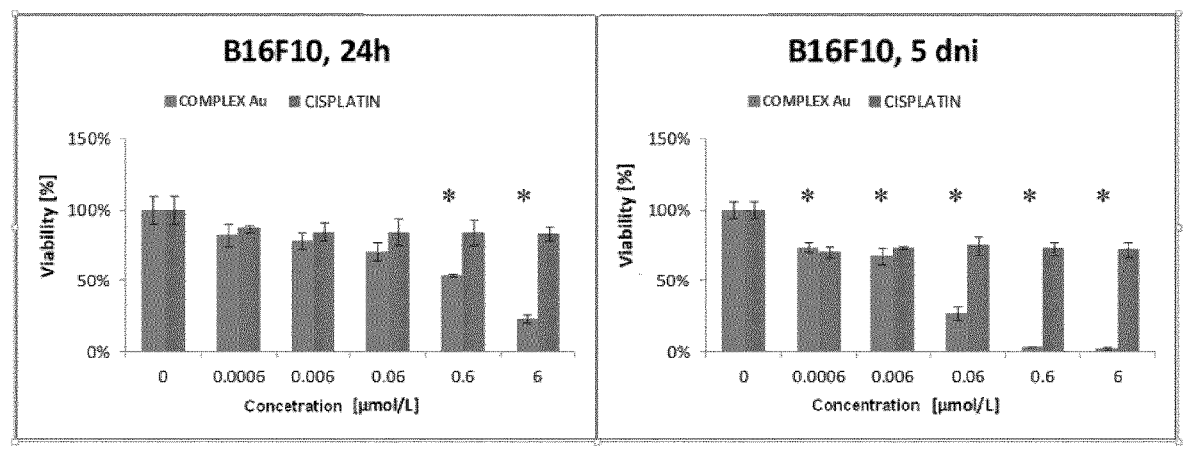
FIG. 3: Viability of the murine melanoma cell line (B16F10) following different incubation periods (24 hours and 5 days) with TGS 21 (see example 2, referred to as "COMPLEX Au" in the figure) compared to cisplatin. The viability is shown in the y-axis. The experiment is described in example 8.

The studies conducted on the B16-F10 murine melanoma cell line demonstrated a significantly higher biological activity towards the cells than cisplatin used in the same range of concentration, as can be derived from FIG. 3. Similarly to the human line (MeWo), they demonstrated sensitivity to the gold compound. Growth inhibition was observed already after 24 hours of incubation for the concentrations of 6 and 0.6 µmol/L. Particularly interesting are the results obtained after 5 days of incubation, which reveal that the gold (III) complex demonstrated also activity at the lowest studied concentration, 0.0006 µmol/L. The concentration inhibiting the growth of 50% of cells for the studied compound is between 0.6-6 µmol/L (for 24-hour incubation). In this case also cisplatin, which is the reference substance, in the studied concentration range demonstrates a weak inhibitory effect.

Both human (MeWo) and murine (B16F10) line cells demonstrated a similar sensitivity to the gold compound.

Example 9

Figure 4:
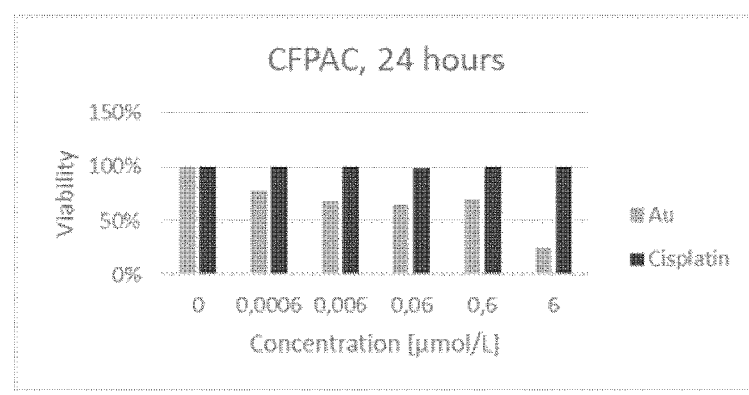
FIG. 4: Viability of the human CFPAC pancreatic cancer cell line following incubation for 24 h with TGS 21 (see example 2, referred to as "Au" in the figure) compared to cisplatin. The experiment is described in example 9.

Viability Test for the CFPAC-1 Pancreatic Cancer Line Following the Administration of Gold (III) Complex
The Application of Mono-Ion Gold (III) Complex (TGS 21) in an Anti-Neoplastic Therapy as Illustrated by the Case of CFPAC-1 Line of Pancreatic Cancer CFPAC-1 cells were incubated either with TGS 21 or cisplatin as indicated in FIG. 4, and the viability was determined as described in example 6. Cells were grown according to standard conditions.

After 24-hour incubation, a statistically significant reduction of viability in the entire concentration range was demonstrated, along with resistance to cisplatin at the same concentrations (see FIG. 4). IC50 for the studied complex is within the range of 0.6-6 µmol/L.

Example 10

Study on the Effect of the New Gold (III) Complex in a Murine Model of Colorectal Cancer
The Application of the New Mono-Ion Gold (III) Complex (TGS 21) in an Anti-Neoplastic Therapy as Illustrated by the Case of Murine Model of Large Intestine and Colorectal Cancer.

Preliminary studies indicated an antineoplastic effect of the studied compound following the oral administration two times a week (8.4 µg in a volume of 100 µl/mouse [i.e. concentration of 0.084 mg/ml)) in a murine model of the colorectal cancer induced by a chronic inflammation.

In the first day of the experiment, the mice received azoxymethane (referred to as "AOM" below, a carcinogenic substance which causes guanine mutations, and is metabolised in the liver) at a dose of 10 mg/kg, administered intraperitoneally.

A week later, the mice were given dextran sodium sulfate solution [DSS] (1.5% w/v) in bottles instead of drinking water. DSS increases intestinal permeability.

After another week, DSS was switched back to normal drinking water for the next 3 weeks.

Three cycles of dextran sodium sulfate/water were conducted before the administration of either AOM/DSS or AOM/DSS+TGS 21 took place (in the amount as stated above, namely 8.4 µg/mouse). The control group did not receive AOM or AOM/DSS.

Administration of Compounds:
   Control group comprising 14 mice (saline)
   AOM/DSS group comprising 13 mice
   AOM/DSS+TGS21 group comprising 21 mice (8.4 µg TGS 21 in 100 µl per os)

The mice were treated for 13 weeks with the oral administration of the actives as outlined above two times a week (with a three to four day interval) using a standard laboratory protocol. The mice were sacrificed after the 13 weeks and the tumor and the spleen were prepared according to standard protocols. The methodology used in the present study is generally e.g. described in Wei T T et al., "*Prevention of Colitis and Colitis-Associated Colorectal Cancer by a Novel Polypharmacological Histone Deacetylase Inhibitor*". Clin Cancer Res. 2016 Aug. 15; 22(16):4158-69. doi: 10.1158/1078-0432.CCR-15-2379.

Spleen weight and percentage proportion of the lesion length to the entire colon length are parameters used to assess neoplastic lesions in the colon. Increased spleen weight indicates an increased activity of immune cells.

Figure 5:
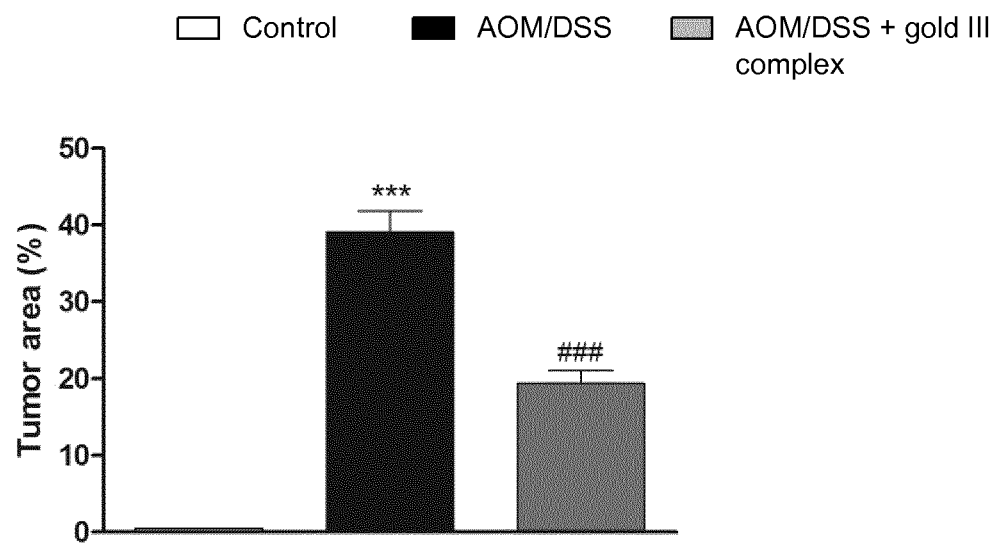
FIG. 5: Tumour area—the proportion of the lesion length to the entire colon length. The left bar is the control, the middle bar is the AOM/DSS-group, and the right bar is the AOM/DSS+TGS 21 group (referred to as "gold III complex" in the figure)—see example 10 for further details.
Figure 6:
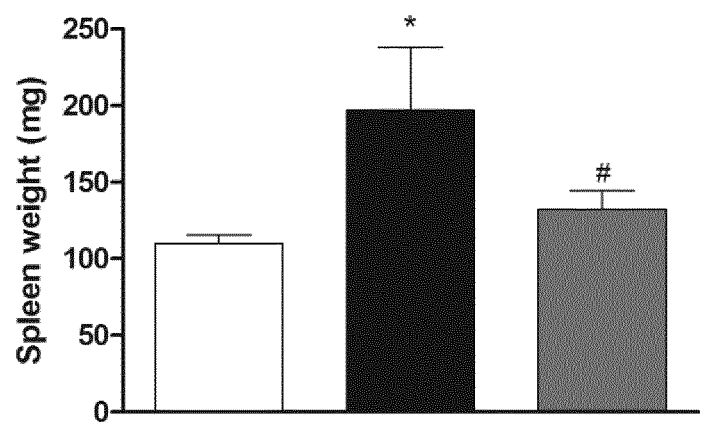
FIG. 6: Spleen weight (mg) of the sacrificed mice is given. The left bar is the control, the middle bar is the AOM/DSS-group, and the right bar is the AOM/DSS+TGS 21 group (see example 10 for further details).

FIGS. 5 and 6 show the results with respect to the area of the tumor and the weight of the spleen.

The results show that the spleen weight is reduced following the administration of TGS 21, and the proportion of the lesion length to the entire colon length is smaller.

Overall, the study showed an anticancer activity of TGS21 in the model used: the number of lesions was lower in mice treated with TGS and the clinical score in these mice indicated milder disease course. The obtained data suggests high therapeutic potential of TGS21.

Example 11

Studies on the MDA Human Breast Cancer Cell Line (MDA-MB-231) Following the Administration of a Gold (III) Complexes: Application of Mono-Ion Gold (III) Complex Prepared with Magnesium Cyanide (an Alkali Earth Metal Cyanide) [TGS 20] Vs. The Application of Monoionic Gold (III) Prepared with Sodium Cyanide (an Alkali Metal Cyanide) [TGS I]

The gold (III) complexes obtained in accordance with examples 1 (TGS20, complex according to the present invention) and example 5 (TGS I, a reference compound) were compared in terms of influence on the neoplastic cell line of MDA-MB-231 viability. To this aim, the complexes were added to cells, which were seeded and cultured under standard conditions (briefly, the cells were cultivated in Leibovitz's L-15 medium supplemented with 2 mM glutamine and 15% foetal bovine serum (FBS) at 37° C.) in multi-well plates. The viability was determined using the standard assay described in example 6 (the seeding density is at $1-3 \times 10^4$ cells/cm$^2$).

Figure 7:
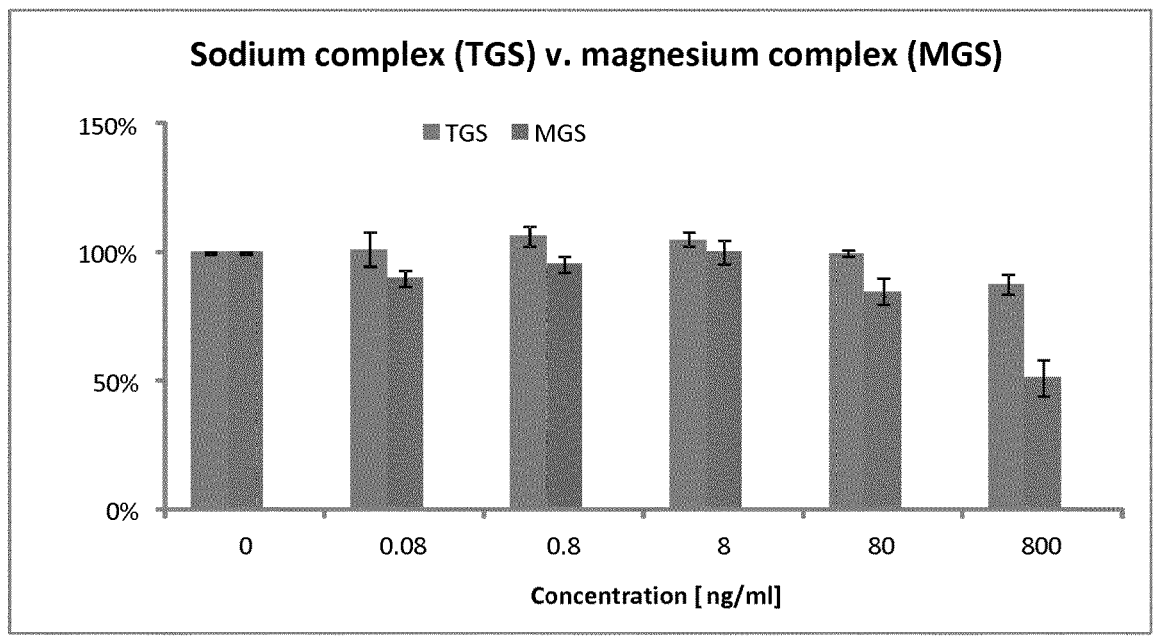
FIG. 7: Viability of breast cancer cell line MDA-MB-231 following incubation with TGS 20 (see example 1, referred to as "magnesium complex, MGS" in the figure) and TGS I (see example 5, referred to as "Sodium complex, TGS" in the figure).

FIG. 7 shows the results at different concentrations of the two complexes, wherein all assays were incubated for 48 hours. The mono-ion gold (III) complex containing magnesium—TGS 20—showed higher inhibition of neoplastic cell line growth compared to the mono-ionic gold (III) complex containing sodium—TGS I—at all concentrations tested, in particular at a concentration of 800 ng/ml.

FIG. 7 shows the advantage of the mono-ion gold (III) complex with magnesium obtained in example 1. The presence of magnesium (an alkaline earth metal from group II of the periodic table) in the structure of the complexes, compared with sodium (alkali metal from group I of the periodic table), has a positive influence on the efficiency of the new compounds.

Example 12

Study on the Effect of the New Gold (III) Complex in a Murine Model of Colorectal Cancer
The Application of the New Mono-Ion Gold (III) Complex (TGS 20) in an Anti-Neoplastic Therapy as Illustrated by the Case of Murine Model of Large Intestine and Colorectal Cancer.

To study the anti-cancer effect of TGS20, the well-established mouse model of colitis-associated colorectal cancer (CACRC), wherein azoxymethane (AOM, given i.p.) is used as a carcinogen and dextran sulfate sodium (DSS, in drinking water) is a pro-inflammatory factor. This model was also used in example 10 of the present application, wherein the present example was carried out over a course of 14 weeks.

Administration of Compounds:

Control group comprising 10 mice (saline over the complete 14 weeks)

AOM/DSS group comprising 18 mice (AOM/DSS over the complete 14 weeks)

AOM/DSS+TGS20 group comprising 18 mice: the mice received AOM/DSS over the first 10 weeks and then for the remaining 4 weeks the mice additionally received TGS20 on every third day in an amount of 0.42 µg TGS 20 in 100 µl per os The mice were treated according to the above dosage regimen using a standard laboratory protocol. The mice were sacrificed after the 14 weeks and the tumor and the colon were prepared according to standard protocols. The methodology used in the present study is generally e.g. described in Wei T T et al., "*Prevention of Colitis and Colitis-Associated Colorectal Cancer by a Novel Polypharmacological Histone Deacetylase Inhibitor*". Clin Cancer Res. 2016 Aug. 15; 22(16):4158-69. doi: 10.1158/1078-0432.CCR-15-2379.

Figure 8:
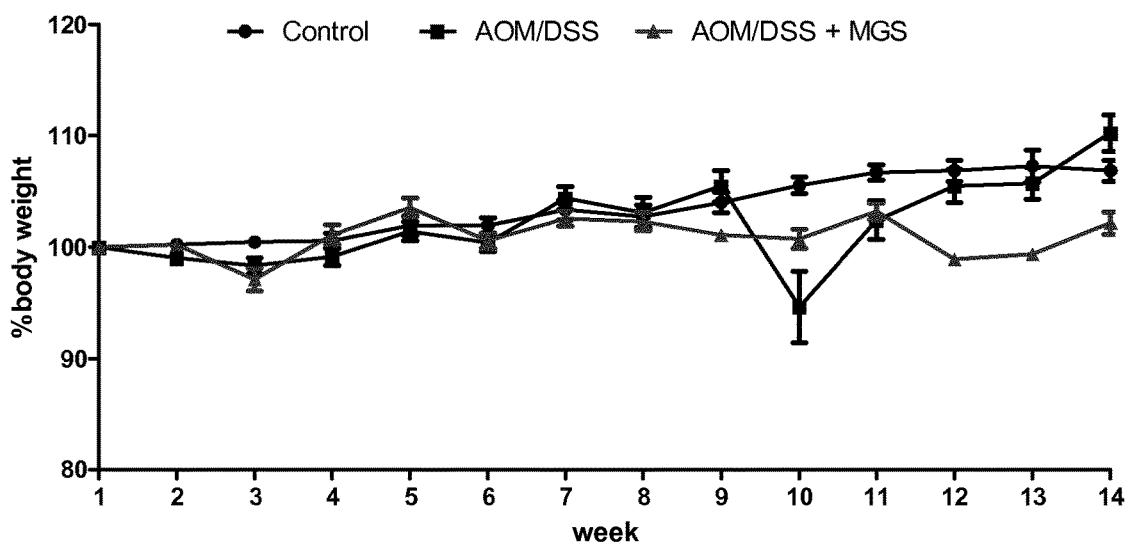
FIG. 8: The boy weight change in % is given for the three groups of mice as indicated in example 12 for the course of the experiment over 14 weeks. TGS 20 (referred to as "MGS" in the figure) was administered as described in example 12 in the third group of mice.

In animals treated with the AOM/DSS combination, a sudden drop of body weight (BW) was observed at week 10 compared with the control, wherein the difference in BW between AOM/DSS and the control group was observed until week 14 (see FIG. 8). Animals treated with AOM/DSS, in which MGS was administered every 3 days starting at week 10 (see above third group of mice), were less prone to BW changes at week 10 onwards than those from AOM/DSS treated group.

Figure 9:
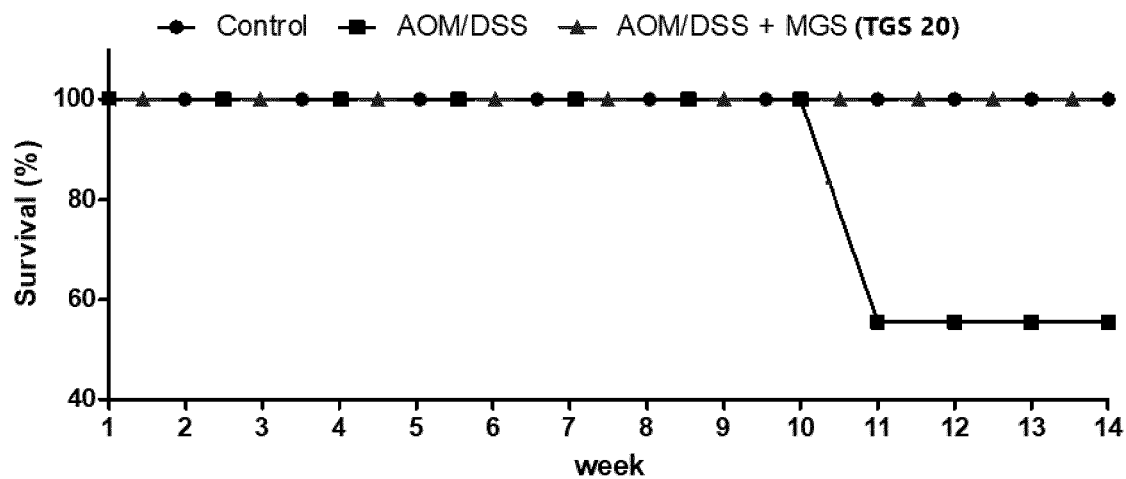
FIG. 9: The survival in % is given for the three groups of mice as indicated in example 12 for the course of the experiment over 14 weeks. TGS 20 (referred to as "MGS" in the figure) was administered as described in example 12 in the third group of mice.

There was also a drop in survival rate for the AOM/DSS treated group, which again continued until week 14 (see FIG. 9).

Figure 10:
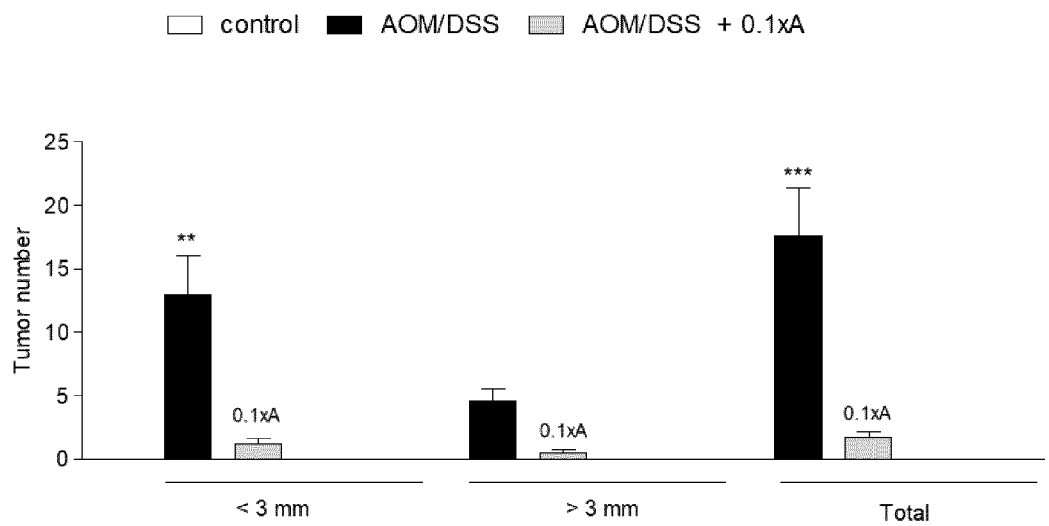
FIG. 10: The tumor numbers observed in the large intestine are indicated, wherein the tumors were divided according to their size: diameter less than 3 mm, greater than 3 mm and total number of tumors. In each group, the left bar is the AOM/DSS-group, the middle bar is the AOM/DSS+TGS 20 group (referred to as "AOM/DSS+0.1×A" in the figure), and the right bar is the control—see example 12 for further details.
Figure 11:
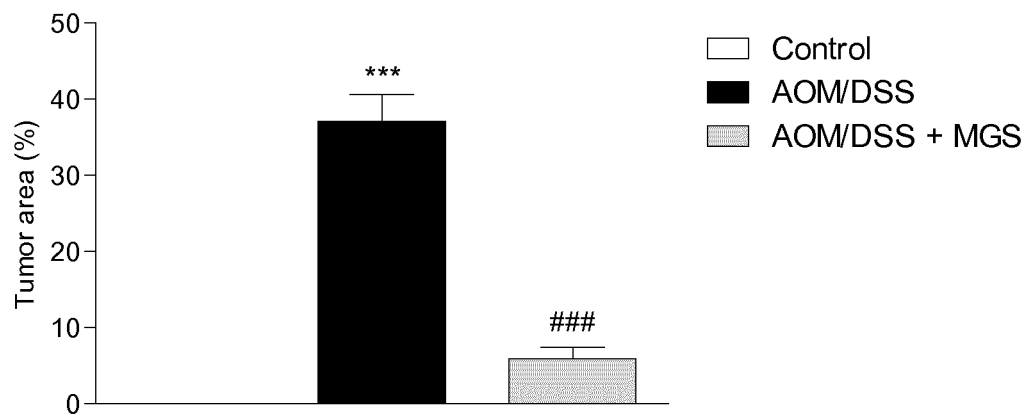
FIG. 11: Tumour area—the proportion of the lesion length to the entire colon length. The left bar is the control, the middle bar is the AOM/DSS-group, and the right bar is the AOM/DSS+TGS 20 (referred to as "MGS" in the figure) group—see example 12 for further details.
Figure 12A:
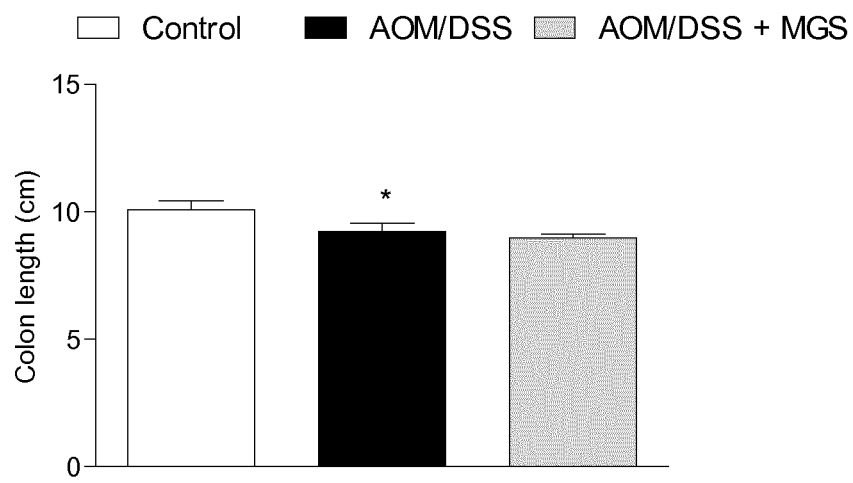
FIG. 12: Colon length (FIG. 12A), colon thickness (FIG. 12B) and colon width (FIG. 12C) after the different treatments: The left bar is the control, the middle bar is the AOM/DSS-group, and the right bar is the AOM/DSS+TGS 20 (referred to as "MGS" in the figure) group—see example 12 for further details.
Figure 12B:
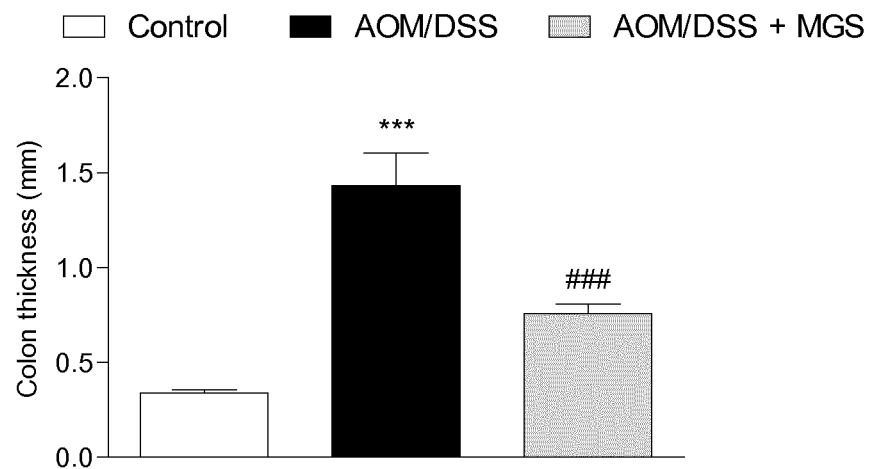
Figure 12C:
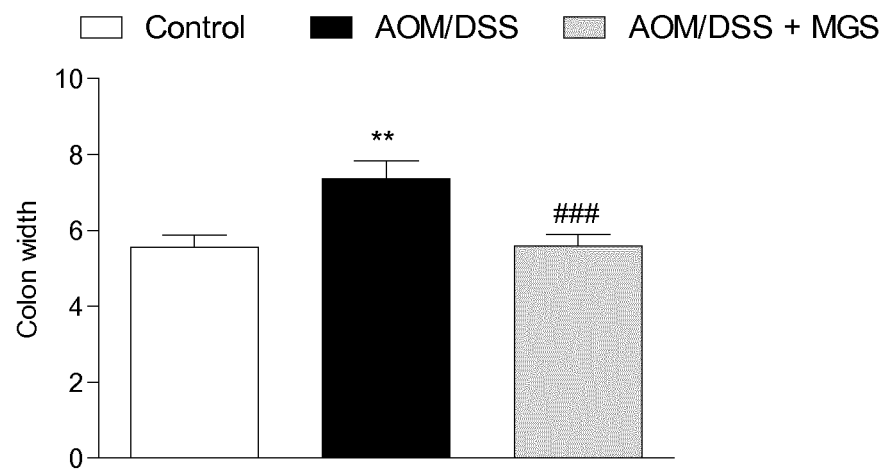

Treatment with AOM/DSS induced a strong cancerogenic effect, which was evidenced by a significant increase in total tumor number (see FIG. 10, p<0.001, vs. healthy controls) and tumor area (see FIG. 11, p<0.001, vs. healthy controls) in the colon. Additional administration of TGS20 from week 10 to week 14 (every third day) decreased significantly the number of tumors (see FIG. 10, p<0.001, depending on tumor area, vs. AOM/DSS treated group) and tumor area (see FIG. 11, p<0.001, depending on the dose, vs. AOM/DSS treated group). Notably, TGS20 attenuated macroscopic inflammation score, as evidenced by increased colon length, thickness and width (see FIGS. 12 A-C, p<0.001-p<0.05, depending on the parameter, vs. AOM/DSS treated group).

Overall, the study showed an anticancer activity of TGS20 in the model used. The obtained data suggests high therapeutic potential of TGS20.

Example 13

The Application of the New Gold (III) Complex in the Production of a Cosmetic Product, Body-Care Gel 400 ml of distilled water was added to a 500 ml beaker, heated to 60° C. 100 g of extract prepared in compliance with example 1 was added. A mechanical stirrer was switched on and 1% of xanthan gum, 10 g of B3 vitamin and 10 g of B5 vitamin were added. The lot was mixed until the liquid was uniform and a clarified gel with well-assimilable gold complex (III) for the application in cosmetic products was obtained.

Example 14

The Application of the New Gold (III) Complex in the Production of Dietary Supplements 450 ml of distilled water was added to a 500 ml beaker, together with 50 g of extract prepared in compliance with example 2. The lot was then heated to 70° C. and a mechanical stirrer was switched on. The clarified extract thus obtained may be applied as a dietary supplement that is source of gold (III) with high bioavailability.

Preliminary studies for the gold (III) complex indicate a high biological activity of the complex towards the neoplastic line. The unquestionable advantages of the new compound include its activity in small concentrations and good solubility in water. The conclusions from the above study may constitute the basis for new medicinal products demonstrating antineoplastic effect and/or preventing the development of neoplasms, as well as for new cancer treatment methods. Presently, they are a subject of intensive further research.

Certain embodiments of the present invention relate to:
1. According to the invention, water soluble, intelligent gold (III) complexes are represented by a general formula:

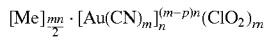

$$[Me]_{\frac{mn}{2}} \cdot [Au(CN)_m]_n^{(m-p)n}(ClO_2)_m$$

where Me represents an alkaline metal belonging to group II of the periodic table, preferably calcium or magnesium, m has the value from 3 to 6, n has the value from 1 to 10, p has the value from 1 to 3, and r has the value from 0.1 to 2.

2. The manner of obtaining water-soluble, intelligent gold complexes (III), which consists in multiple extracting of chemical clusters of gold in hydrochloric acid (HCl), in the presence of at least 10 mol excess of monovalent alkaline metal chlorides, and vaporisation until clusters of less than 1 nanometer are obtained, i.e. mono-ions of di-ions of gold (III), characterised by the fact that in the aqueous or hydroalcoholic solution the obtained mono-ions or di-ions of gold (III) react with a cyanide of a divalent alkaline metal belonging to group II of the periodic table, preferably calcium or magnesium, in a molar ratio of 2:3 to 1:3, preferably in presence of a mild oxidiser, such as a chloride dioxide (IV), or its predecessor sodium chlorite (III) used in the molar ratio of 0.1 to 2 in relation to gold (III).

3. The application of water soluble intelligent gold complexes (III) with the above formula in the production of pharmaceuticals or components to pharmaceuticals, in the production of cosmetics or components of cosmetics, or in the production of dietary supplements or components of dietary supplements, as well as application in the treatment of neoplasms at a chosen dosage and therapeutically justified amount.

More preferred embodiments of the present invention relate to:
1. A process for the preparation of a composition comprising a gold(+III) compound comprising the steps of:
a) mixing a mixture A comprising a digold(+III) halide and/or gold(+III) halide with a mixture B comprising an alkali halide to create a product mixture 1 or providing commercially available NaAuCl$_4$ and mixing the same with water in order to obtain a product mixture 1;

b) mixing product mixture 1 with hydrochloric acid to create a product mixture 2;
c) adjusting the pH of product mixture 2 to a pH value of from 2 to 7;
d) mixing product mixture 2 with a mixture C comprising an alkali chlorite to create a product mixture 3;
e) adjusting the pH of product mixture 3 to an pH of from 5 to 9;
f) mixing product mixture 3 with a mixture D comprising an alkaline earth cyanide to create a product mixture 4;
g) mixing product mixture 4 with an acid to create a product mixture 5, and subjecting product mixture 5 to reduced pressure; and
h) adjusting the pH of product mixture 5 to a value of 7 to 8 to obtain a composition comprising a gold(+III) compound.

2. The process according to embodiment 1, wherein the digold(+III) halide is a digold(+III) chloride, and/or wherein the gold(+III) halide is gold(+III) chloride, and/or wherein the alkali halide is sodium chloride.

3. The process according to embodiment 1 or 2, wherein the mixing of mixture A with mixture B of step a) is effected over a time period of from 1 min to 48 h, preferably from 1 h to 24 h, and more preferably from 5 h to 18 h, and most preferably from 8 h to 12 h, and/or wherein the mixing of step a) is effected at a reaction temperature of from 20° C. to 200° C., preferably from 50° C. to 150° C., most preferably from 80° C. to 120° C.

4. The process according to any one of the preceding embodiments, wherein step a) further comprises step a1) of admixing water to mixture A and/or mixture B, and/or wherein mixture A and/or mixture B further comprise water.

5. The process according to embodiment 4, wherein step a) further comprises a step a2) of evaporating the water of product mixture 1 to obtain a product mixture 1A.

6. The process according to any one of the preceding embodiments, wherein the hydrochloric acid of step b) is an aqueous solution of hydrochloric acid having a concentration of from 0.1M to 12M, preferably of 2M to 10M, and most preferably of from 5M to 7M.

7. The process according to embodiment 6, wherein step b) further comprises a step b1) of evaporating the water of product mixture 2 to obtain a product mixture 2A, and a step b2) of adding water to product mixture 2A to obtain a product mixture 2B.

8. The process according to any one of the preceding embodiments, wherein the pH is adjusted in step c) with a hydroxide base, preferably sodium or potassium hydroxide, and/or wherein the pH is adjusted to a value of from 3 to 6, and preferably from 4 to 5.

9. The process according to any one of the preceding embodiments, wherein the alkali chlorite of mixture C is sodium chlorite, and/or wherein the amount of alkali chlorite used in mixture C and the amount of the gold(+III) compound(s) used in mixture A have a molar ratio of from 10:1 to 1:2, preferably from 5:1 to 1:1, and most preferably from 3:1 to 1.5:1.

10. The process according to any one of the preceding embodiments, wherein mixture C further comprises water and the alkali chlorite is present in a weight amount of 0.1 wt. % to 10 wt. %, preferably from 0.5 wt. % to 5 wt. %, and most preferably from 0.5 wt. % to 3 wt. %, based on the total weight of mixture C.

11. The process according to any one of the preceding embodiments, wherein the alkaline earth cyanide of mixture D is selected from the group consisting of magnesium cyanide, calcium cyanide, or a mixture thereof, preferably wherein the alkaline earth cyanide of mixture D is magnesium cyanide, and/or wherein mixture D further comprises water and/or an organic solvent.

12. The process according to embodiment 11, wherein mixture D has a concentration of alkaline earth cyanide of from 0.01M to 5M, preferably of 0.01M to 2M, and most preferably of from 0.03M to 1.2M, and/or wherein the amount of alkaline earth cyanide used in mixture D and the amount of the gold(+III) compound(s) used in mixture A have a molar ratio of from 10:1 to 1:2, preferably from 6:1 to 1:1, and most preferably from 4:1 to 2:1.

13. A composition comprising a gold(+III) compound, obtainable by the process according to any one of embodiments 1 to 12.

14. A composition comprising a gold(+III) compound according to embodiment 13 for use in therapy.

15. A composition comprising a gold(+III) compound according to embodiment 13 for use in the treatment of cancer, preferably colon cancer.

The invention claimed is:
1. A process for the preparation of a composition comprising a gold(+III) compound comprising the steps of:
a) providing a mixture A comprising a tetrachloroaurate salt,
b) mixing the composition of step a) with a mixture B comprising a chlorite salt;
c) mixing the composition obtained in step b) with a mixture C comprising an alkaline earth cyanide to obtain a composition comprising a gold (+III) compound.

2. The process according to claim 1, wherein step a) additionally includes mixing said mixture A comprising a tetrachloroaurate salt with hydrochloric acid, wherein said hydrochloric acid is an aqueous solution of hydrochloric acid having a concentration of from 0.1M to 12M.

3. The process according to claim 1, wherein the tetrachloroaurate salt of mixture A is an alkali tetrachloroaurate salt, and/or wherein mixture A further comprises an alkali halide, and/or wherein the molar ratio of the alkali halide to the tetrachloroaurate salt is at least 100.

4. The process according to claim 2, wherein the process further comprises a step a1) of evaporating the water of the composition obtained in step a), and a step a2) of adding water to the composition obtained in step a1).

5. The process according to any one of claim 4, wherein the process further comprises a step a3) of adjusting the pH of the composition obtained in step a), a1) or a2) to a pH value of from 2 to 7 using a hydroxide base.

6. The process according to claim 1, wherein the chlorite salt of mixture B is an alkali chlorite, and/or wherein the amount of chlorite salt used in mixture B and the amount of the gold(+III) compound used in mixture A have a molar ratio of from 10:1 to 1:2.

7. The process according to claim 1, wherein mixture B further comprises water and/or the chlorite salt is present in mixture B in a weight amount of 0.1 wt. % to 10 wt. % based on the total weight of mixture B.

8. The process according to claim 1, wherein the process further comprises a step b1) of adjusting the pH of the composition obtained in step b) to an pH value of from 5 to 9 using a carbonate base.

9. The process according to claim 1, wherein the alkaline earth cyanide of mixture C is selected from the group of magnesium cyanide, calcium cyanide, and mixtures thereof, and/or wherein mixture C further comprises water, an organic solvent, or a mixture thereof.

10. The process according to claim 9, wherein mixture C has a concentration of alkaline earth cyanide of from 0.01M to 5M, and/or wherein the amount of alkaline earth cyanide used in mixture C and the amount of the gold(+III) compound used in mixture A have a molar ratio of from 10:1 to 1:2.

11. The process according to claim 1, wherein the process further comprises a step d) of mixing the composition obtained in step c) with an acid, and/or subjecting the composition obtained in step c) to reduced pressure.

12. The process according to claim 11, wherein the process further comprises a step e) of adjusting the pH of the composition obtained in step c) or d) to a value of from 7 to 8.

13. The process according to claim 3, wherein the alkali tetrachloroaurate salt is sodium tetrachloroaurate or a hydrated version thereof, and wherein the alkali halide is sodium chloride.

14. The process according to claim 5, wherein the adjusting the pH of the composition obtained in step a), a1) or a2) is from 4 to 5, wherein the hydroxide base is chosen from sodium or potassium hydroxide.

15. The process according to claim 6, wherein the alkali chlorite is sodium chlorite.

16. The process according to claim 9, wherein the alkaline earth cyanide is magnesium cyanide.

* * * * *